United States Patent
Grubac et al.

(10) Patent No.: US 12,179,016 B2
(45) Date of Patent: Dec. 31, 2024

(54) FIXATION COMPONENT FOR MULTI-ELECTRODE IMPLANTABLE MEDICAL DEVICE

(71) Applicant: Medtronic, Inc., Minneapolis, MN (US)

(72) Inventors: Vladimir Grubac, Brooklyn Park, MN (US); Jeffrey S. Voss, White Bear Lake, MN (US); Allison E. Winans, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 345 days.

(21) Appl. No.: 17/648,607

(22) Filed: Jan. 21, 2022

(65) Prior Publication Data

US 2022/0257933 A1 Aug. 18, 2022

Related U.S. Application Data

(60) Provisional application No. 63/149,594, filed on Feb. 15, 2021.

(51) Int. Cl.
*A61N 1/05* (2006.01)
*A61N 1/375* (2006.01)

(52) U.S. Cl.
CPC ....... *A61N 1/0573* (2013.01); *A61N 1/37512* (2017.08); *A61N 2001/0578* (2013.01); *A61N 2001/058* (2013.01)

(58) Field of Classification Search
CPC .............. A61N 1/0573; A61N 1/37518; A61N 1/0558; A61N 1/059
See application file for complete search history.

(56) References Cited

U.S. PATENT DOCUMENTS 3,814,104 A * 6/1974 Irnich ................ A61N 1/0573
607/128
3,943,936 A 3/1976 Rasor et al.
(Continued)

FOREIGN PATENT DOCUMENTS

DE 202019105583 U1 11/2019
WO 2002022202 A2 3/2002
(Continued)

OTHER PUBLICATIONS

International Search Report and Written Opinion of International Application No. PCT/US2020/045857, mailed Nov. 6, 2020, 8 pp.
(Continued)

*Primary Examiner* — Eric D. Bertram
(74) *Attorney, Agent, or Firm* — Shumaker & Sieffert, P.A.

(57) ABSTRACT

An implantable medical device (IMD) includes a body, a fixation component, and an interface assembly. The body extends from a proximal portion to a distal portion along a longitudinal axis. The fixation component includes a penetrator tine. The penetrator tine includes an incisive distal end configured to penetrate a tissue to fix the IMD to the tissue. The electrode interface assembly includes a proximal section and a distal section. The proximal section is attached to and extends distally from the distal portion of the body along the longitudinal axis. The distal section extends from the proximal section of the electrode interface assembly and defines a non-incisive distal end. The distal end of the electrode interface assembly is configured to contact the tissue to control a depth of tissue penetration of the penetrator tine.

22 Claims, 15 Drawing Sheets

(56) References Cited

U.S. PATENT DOCUMENTS

| | | | |
|---|---|---|---|
| 4,103,690 | A | 8/1978 | Harris |
| 4,142,530 | A | 3/1979 | Wittkampf |
| 4,269,198 | A | 5/1981 | Stokes |
| 4,280,512 | A | 7/1981 | Karr et al. |
| 4,590,949 | A | 5/1986 | Pohndorf |
| 4,858,623 | A | 8/1989 | Bradshaw et al. |
| 4,936,823 | A | 6/1990 | Colvin |
| 5,193,540 | A | 3/1993 | Schulman et al. |
| 5,411,535 | A | 5/1995 | Fujii et al. |
| 5,573,540 | A | 11/1996 | Yoon |
| 5,683,447 | A | 11/1997 | Bush et al. |
| 6,007,558 | A | 12/1999 | Ravenscroft et al. |
| 6,151,525 | A | 11/2000 | Soykan et al. |
| 6,240,322 | B1 | 5/2001 | Peterfeso et al. |
| 6,286,512 | B1 | 9/2001 | Loeb et al. |
| 6,409,674 | B1 | 6/2002 | Brockway et al. |
| 6,575,967 | B1 | 6/2003 | Leveen et al. |
| 6,783,499 | B2 | 8/2004 | Schwartz |
| 6,915,149 | B2 | 7/2005 | Ben-Haim |
| 6,978,178 | B2 | 12/2005 | Sommer et al. |
| 7,290,743 | B2 | 11/2007 | Nowack |
| 7,418,298 | B2 | 8/2008 | Shiroff et al. |
| 8,353,940 | B2 | 1/2013 | Benderev |
| 9,526,522 | B2 | 12/2016 | Wood et al. |
| 10,099,050 | B2 | 10/2018 | Chen et al. |
| 11,684,776 | B2 * | 6/2023 | Grubac .................. A61B 5/686 600/509 |
| 2002/0103424 | A1 | 8/2002 | Swoyer et al. |
| 2002/0165589 | A1 | 11/2002 | Imran et al. |
| 2003/0088301 | A1 | 5/2003 | King |
| 2004/0147973 | A1 | 7/2004 | Hauser |
| 2004/0230281 | A1 | 11/2004 | Heil et al. |
| 2006/0084965 | A1 | 4/2006 | Young |
| 2006/0085039 | A1 | 4/2006 | Hastings et al. |
| 2006/0085041 | A1 | 4/2006 | Hastings et al. |
| 2007/0021813 | A1 | 1/2007 | Sommer et al. |
| 2007/0135883 | A1 | 6/2007 | Drasler et al. |
| 2009/0082828 | A1 | 3/2009 | Ostroff |
| 2011/0270340 | A1 | 11/2011 | Pellegrini et al. |
| 2012/0172892 | A1 | 7/2012 | Grubac et al. |
| 2014/0039591 | A1 | 2/2014 | Drasler et al. |
| 2015/0039070 | A1 | 2/2015 | Kuhn et al. |
| 2015/0039071 | A1 | 2/2015 | Grubac et al. |
| 2015/0045868 | A1 | 2/2015 | Bonner et al. |
| 2016/0059003 | A1 * | 3/2016 | Eggen .................... A61N 1/057 606/129 |
| 2017/0106185 | A1 | 4/2017 | Orts et al. |
| 2017/0209688 | A1 | 7/2017 | Drake et al. |
| 2017/0209689 | A1 | 7/2017 | Chen et al. |
| 2018/0050208 | A1 | 2/2018 | Shuros et al. |
| 2018/0207434 | A1 | 7/2018 | Webb et al. |
| 2018/0280686 | A1 | 10/2018 | Shuros et al. |
| 2019/0054288 | A1 | 2/2019 | Grubac et al. |
| 2019/0083779 | A1 | 3/2019 | Yang et al. |
| 2019/0083801 | A1 | 3/2019 | Yang et al. |
| 2019/0192863 | A1 | 6/2019 | Koop et al. |
| 2020/0306522 | A1 | 10/2020 | Chen et al. |
| 2020/0306530 | A1 | 10/2020 | Koop et al. |
| 2020/0338356 | A1 * | 10/2020 | Anderson ............... A61N 1/056 |
| 2020/0353242 | A1 | 11/2020 | Drake et al. |
| 2021/0046306 | A1 * | 2/2021 | Grubac .................. A61N 1/362 |
| 2021/0069491 | A1 | 3/2021 | Grubac et al. |
| 2021/0236814 | A1 | 8/2021 | Anderson et al. |
| 2021/0275824 | A1 | 9/2021 | Rock et al. |
| 2022/0062630 | A1 | 3/2022 | Yang et al. |
| 2023/0012417 | A1 * | 1/2023 | Rock .................. A61N 1/37205 |
| 2023/0098146 | A1 * | 3/2023 | Rock .................... A61N 1/3756 607/2 |
| 2023/0271000 | A1 * | 8/2023 | Grubac .................. A61B 5/686 600/509 |

FOREIGN PATENT DOCUMENTS

| | | |
|---|---|---|
| WO | 2006118865 A2 | 11/2006 |
| WO | 2021030392 A1 | 2/2021 |

OTHER PUBLICATIONS

U.S. Appl. No. 16/990,239, filed Aug. 11, 2020, naming inventors Grubac et al.

U.S. Appl. No. 16/847,315, filed Apr. 13, 2020, naming inventors Drake et al.

U.S. Appl. No. 16/825,143, filed Mar. 20, 2020, naming inventors Chen et al.

Notice of Allowance from U.S. Appl. No. 16/990,239 dated Oct. 19, 2022, 10 pp.

Response to Final Office Action dated Jul. 27, 2022 from U.S. Appl. No. 16/990,239, filed Sep. 22, 2022, 18 pp.

Haqqani et al., "The Implantable Cardioverter-Defibrillator Lead: Principles, Progress and Promises," PACE, vol. 32, Oct. 2009, pp. 1336-1353.

Office Action from U.S. Appl. No. 16/990,239, dated Mar. 2, 2022, 13 pp.

Response to Office Action dated Mar. 2, 2022, from U.S. Appl. No. 16/990,239, filed Jun. 2, 2022, 20 pp.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

Final Office Action from U.S. Appl. No. 16/990,239, dated Jul. 27, 2022, 26 pp.

Notice of Allowance from U.S. Appl. No. 16/990,239 dated Feb. 10, 2023, 8 pp.

\* cited by examiner

FIXATION COMPONENT FOR MULTI-ELECTRODE IMPLANTABLE MEDICAL DEVICE

This application claims the benefit of U.S. Provisional Patent Application Ser. No. 63/149,594, filed Feb. 15, 2021, the entire content of which is incorporated herein by reference.

TECHNICAL FIELD

This disclosure is related to medical device systems, such as relatively compact implantable medical devices and associated fixation components.

BACKGROUND

In some examples, implantable cardiac pacemakers include a pulse generator device to which one or more flexible elongate lead wires are coupled. The pulse generator device may be implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues may be associated with elongate lead wires. Relatively compact implantable medical devices (IMDs) have been developed that are wholly contained within a relatively compact package, the entirety of which is configured for implant in close proximity to the pacing site, e.g., within a chamber of the heart.

SUMMARY

This disclosure describes IMDs that include a fixation component with a penetrator tine and an electrode interface assembly. The penetrator tine of the fixation component may operate in conjunction with one or more elongate electrodes (e.g., a leadlet) mounted in proximity to a distal end of an IMD. For example, the penetrator tine may define an exoskeleton of a cardiac pacing electrode. The penetrator tine may operate in conjunction with an electrode interface assembly configured to control a depth of tissue penetration of the penetrator tine. When deployed, the penetrator tine and electrode interface assembly may provide improved tissue fixation, controlled penetration to a selected depth within a tissue, improved electrode tissue interface, and/or improved tissue disengagement compared to fixation components without the described penetrator tine and/or electrode interface assembly. In this way, the fixation component may facilitate implanting and/or extracting IMDs.

In some examples, an IMD includes a body, a fixation component, and an electrode assembly interface. The body extends from a proximal portion to a distal portion along a longitudinal axis. The fixation component includes a base and a penetrator tine. The base has a proximal end and a distal end aligned along the longitudinal axis. The proximal end of the base is attached to the distal portion of the body. The penetrator tine includes a proximal section, a curved section, and a distal section. The proximal section is attached to and extends from the distal end of the base in a first direction. The curved section defines a deformable preset curvature of the penetrator tine and extends in a second direction laterally from the proximal section of the penetrator tine and transverses the longitudinal axis. The distal section extends from the curved section of the penetrator tine and terminates in an incisive distal end. The incisive distal end is configured to penetrate a tissue to fix the IMD to the tissue. The electrode interface assembly includes a proximal section and a distal section. The proximal section includes a proximal end that is attached to and extends distally from the distal portion of the body along the longitudinal axis. The distal section extends from the proximal section of the electrode interface assembly and defines a non-incisive distal end. The non-incisive distal end of the electrode interface assembly is configured to contact the tissue to control a depth of tissue penetration of the penetrator tine.

In some examples, a medical device system includes an IMD and a delivery tool. The IMD includes a body, an elongate leadlet, a return electrode, a fixation component, and an electrode assembly interface. The body extends from a proximal portion to a distal portion along a longitudinal axis. The elongate leadlet extends from a proximal end of the elongate leadlet mounted in proximity to the distal end of the body to a distal end of the elongate leadlet. The distal end of the elongate leadlet includes a first electrode. The return electrode is defined by a nonconductive coating on the body of the IMD. The fixation component includes a base and a penetrator tine. The base has a proximal end and a distal end aligned along the longitudinal axis. The proximal end of the base is attached to the distal portion of the body. The penetrator tine includes a proximal section, a curved section, and a distal section. The proximal section is attached to and extends from the distal end of the base in a first direction. The curved section defines a deformable preset curvature of the penetrator tine and extends in a second direction laterally from the proximal section of the penetrator tine and transverses the longitudinal axis. The distal section extends from the curved section of the penetrator tine and terminates in an incisive distal end. The incisive distal end is configured to penetrate a tissue to fix the IMD to the tissue. The electrode interface assembly includes a proximal section and a distal section. The proximal section includes a proximal end that is attached to and extends distally from the distal portion of the body along the longitudinal axis. The distal section extends from the proximal section of the electrode interface assembly and defines a non-incisive distal end. The non-incisive distal end of the electrode interface assembly is configured to contact the tissue to control a depth of tissue penetration of the penetrator tine. The delivery tool includes a tubular sidewall that defines a lumen into which the IMD is loaded. The lumen includes a distal opening through which the IMD may be deployed.

In some examples, a method of forming an IMD includes forming a body of the IMD, a base of a fixation component, a penetrator tine of the fixation component, and an electrode interface assembly. The body extends from a proximal portion to a distal portion along a longitudinal axis. The base defines a longitudinal axis of the fixation component. The penetrator tine includes a proximal section, a curved section, and a distal section. The proximal section is attached to and extends from the distal end of the base in a first direction. The curved section defines a deformable preset curvature of the penetrator tine and extends in a second direction laterally from the proximal section of the penetrator tine and transverses the longitudinal axis. The distal section extends from the curved section of the penetrator tine and terminates in an incisive distal end. The incisive distal end is configured to penetrate a tissue to fix the IMD to the tissue. The electrode interface assembly includes a proximal section and a distal section. The proximal section includes a proximal end that is attached to and extends distally from the distal portion of the body along the longitudinal axis. The distal section extends from the proximal section of the electrode interface assembly and defines a non-incisive distal end. The non-incisive distal end of the electrode interface assembly is configured to contact the tissue to control a depth of tissue penetration of the penetrator tine.

The details of one or more examples are set forth in the accompanying drawings and the description below. Other features, objects, and advantages will be apparent from the description and drawings, and from the claims.

DETAILED DESCRIPTION

Figure 1:
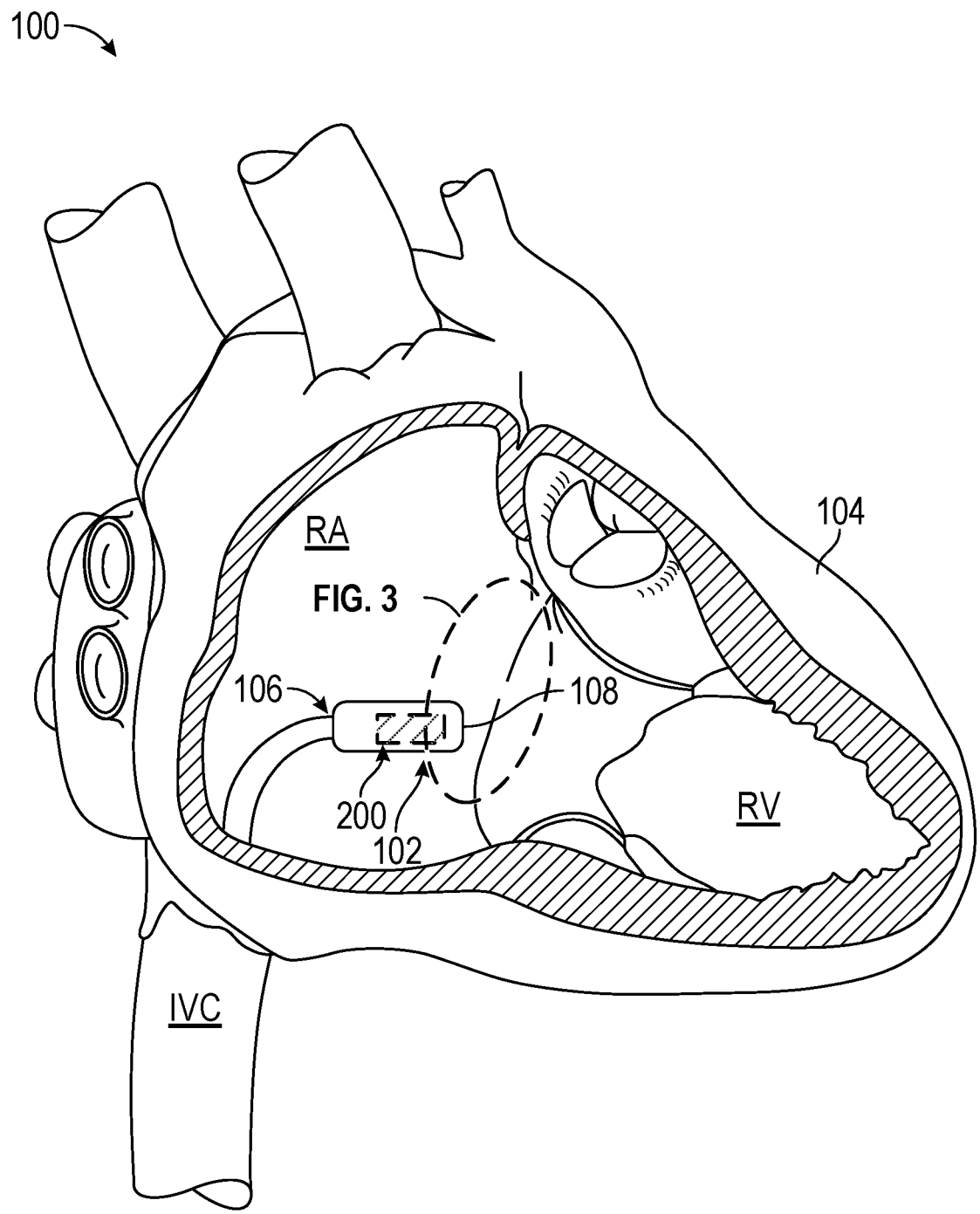
FIG. 1 is a conceptual diagram illustrating a portion of an example medical device system configured to implant a relatively compact implantable medical device at a target implant site.

This disclosure describes implantable medical devices (IMDs), components of IMDs, medical device systems including IMDs, and related techniques of using and forming IMDs. An example IMD may include a body, one or more elongate leadlets, a fixation component that includes a base and a plurality of tines, and an electrode interface assembly (EIA). One or more tines of the fixation component are configured to penetrate a tissue, and EIA is configured to control a depth of tissue penetration of the one or more tines.

In some examples, the body of the IMD may extend along a longitudinal axis from a proximal portion of the body to a distal portion, and may enclose components of the IMD, such as circuitry and a battery. The body of the IMD may support a return electrode configured to allow electrical energy to flow from the tissue to the IMD through the return electrode.

A proximal end of a first leadlet may be mounted to the body, e.g., in proximity to the distal end of the body. The distal end of the first leadlet may include an electrode, such as a first electrode of the IMD. The IMD may include additional electrodes, such as a second electrode included in the EIA, which may or may not be included as part of elongate leadlets extending from the body of the IMD. The electrodes of the IMD may be configured to sense electrical signals from tissue and/or deliver electrical therapies to the tissue.

The fixation component of the IMD may include a base and a plurality of tines. The base may define a longitudinal axis of the fixation component, and a proximal end and a distal end of the IMD may be aligned along the longitudinal axis. The longitudinal axis of the fixation component and IMD may be parallel and, in some cases, the fixation component and IMD may share a longitudinal axis. The base may be fixedly attached to the IMD near the distal end of the IMD. The plurality of tines includes a penetrator tine, and may include additional tines, such as support tines, deployment tines, alignment tines, or protector tines. The plurality of tines may be spaced apart from one another around a perimeter of the distal end of the IMD and extend from the base. A shape of each respective tine of the plurality of tines may be selected to control deployment of the IMD, tissue fixation, and/or tissue disengagement. For example, the shape of a respective tine may include a number of preset curves on the respective tine, a curvature (e.g., radius) of each preset curve on the respective tine, a length of each preset curve, a length of optional straight sections between preset curves, a width of the respective tine or sections thereof (e.g., one or more tapered portions), a thickness of the respective tine, a number of cutouts along the length of the respective tine, shapes of cutouts, or any combination thereof.

The IMD includes an electrode interface assembly (EIA) that may operate in conjunction with the fixation component to control a depth of tissue penetration of one or more tines. For example, the EIA may be configured to contact the tissue, and thus resist further tissue penetration, to control the depth of tissue penetration of the penetrator tine. The EIA may include a proximal section attached to and extending distally from the distal portion of the body of the IMD along the longitudinal axis. The EIA may further include a distal section extending from the proximal section of the EIA and defining a non-incisive distal end. The distal section of the EIA may be configured to contact the tissue to control a depth of tissue penetration of the penetrator tine. For example, the EIA may be formed (e.g., dimensioned) to have a proximal section and distal section with a total length that results in contact between the EIA and the tissue at a selected depth of tissue penetration of the penetrator tine. Additionally or alternatively, the EIA may be positioned on the IMD to result in contact between the EIA and the tissue at a selected depth of tissue penetration of the penetrator tine. In any case, the EIA may be configured to achieve a selected distance between the incisive distal section of the penetrator tine and the distal end of the EIA (e.g., within a range from about 4 millimeters to about 10 millimeters).

When deployed, the plurality of tines, in conjunction with the EIA, may provide a selected tissue fixation. For example, the deformable preset curve of a penetrator tine may have a shape selected to penetrate tissue in a selected direction and a selected depth to fixate the IMD to the tissue. Furthermore, the distal section of the EIA may be configured to contact the tissue when the penetrator tine reaches the selected depth of tissue penetration, resisting further tissue penetration and thus controlling the depth of tissue penetration of the penetrator tine. Similarly, in another example, the deployed (e.g., undeformed) configuration of the penetrator tine, in conjunction with the EIA, may be selected to sufficiently fixate the IMD to the selected tissue.

The IMD may be loaded into a delivery catheter by deforming the deformable preset curvature of each respective tine of the plurality of tines and, optionally, a deformable portion of the EIA. When deployed at a target implant site (e.g., by allowing the tines to transition to the deployed configuration), the tines have a deployment stiffness that enables the tines to penetrate the tissue at a target implant site. By controlling the deployment stiffness, the tines may have improved tissue fixation, including control of a depth of tine penetration and an amount of tissue engagement in a lateral direction.

In some examples, the penetrator tine and the EIA may operate in conjunction with a first leadlet. The penetrator tine may be configured to penetrate or cut a tissue to form a puncture in the tissue. The EIA may be configured to protect the first leadlet during deployment, such as, by applying a force to first leadlet in the direction of the penetrator tine during and/or after deployment, thereby reducing an undesired displacement of the first leadlet or mechanical damage to the structure of the first leadlet. For example, during deployment from the delivery catheter, the penetrator tine may initially penetrate a selected tissue to form a puncture, and EIA may apply a force to the first leadlet, thus urging the first leadlet toward the penetrator tine and guiding the first leadlet into the puncture. As the fixation component is further deployed, the penetrator tine may return from a deformed (e.g., pre-deployment) configuration to (or at least towards) the undeformed (e.g., deployed) configuration. Upon reaching a selected depth of tissue penetration of the penetrator tine, EIA may contact the tissue to resist further tissue penetration.

When the penetrator tine is in the deployed configuration, the first leadlet may extend in a distal direction between the penetrator tine and the EIA, such that the first leadlet extends from the distal end of the body of the IMD to reach the selected target tissue. In this way, the fixation component and the EIA may provide improved electrode penetration to a selected depth within the selected tissue and improved electrode contact with the selected tissue. In some examples, the EIA may include a second electrode configured to operate in a manner similar to the first electrode.

After deployment at the target implant site, a deflection stiffness of the penetrator tine enables a clinician to confirm adequate fixation of the penetrator tine into tissue of a patient. For example, a pull test or a tug test may be performed under fluoroscopy to confirm that the penetrator tine has engaged the tissue to confirm adequacy of implantation of the IMD. The pull test or tug test may include the clinician pulling or tugging on the deployed IMD, e.g., via a tether coupled to a proximal end of the IMD, and observing movement of the penetrator tine to determine if the penetrator tine is engaged in tissue. For example, the penetrator tine that is embedded in tissue may deflect or bend as the deployed IMD is pulled or tugged in the proximal direction. By controlling the deflection stiffness, the penetrator tine may have an improved flexibility that enables a clinician to more easily confirm tissue engagement.

In some examples, the tines may be configured to disengage from the tissue. For example, the IMD may be retrieved by a retrieval catheter. During retrieval, a retrieval member of the retrieval catheter may engage a proximal end of the IMD, such as a retrieval structure. The retrieval member may be withdrawn in a proximal direction into the retrieval catheter. Withdrawing the retrieval member in the proximal direction may cause the tines to move from the undeformed configuration to the deformed configuration as the tissue resists movement of the tines. By moving from the undeformed configuration to the deformed configuration during retrieval, the tines may improve tissue disengagement to facilitate extracting the IMD, compared to tines that do not move from an undeformed configuration to a deformed configuration during retrieval from a tissue.

In this disclosure, the example systems, devices, and techniques will be described with reference to delivering an IMD configured as a cardiac pacemaker to a target site in a heart of a patient. However, it will be understood that example systems, devices, and techniques of the present disclosure are not limited to delivering such IMDs to a target site in the heart. For example, the example systems, devices, and techniques described herein may be used to deliver other medical devices, such as drug delivery device, sensing devices, neurostimulation device, or medical electrical leads. Additionally, the example systems, devices, and techniques described herein may be used to deliver any such IMDs to other locations within a body of a patient. In short, the example systems, devices, and techniques described herein can find useful application in delivery of a wide variety of implantable medical devices for delivery of therapy to a patient or patient sensing.

FIG. 1 is a conceptual diagram illustrating a portion of an example medical device system 100 configured to implant a relatively compact implantable medical device 200 ("IMD 200") at a target implant site 102. In some examples, as illustrated in FIG. 1, the target implant site 102 may include an appendage of a right atrium (RA) of the heart 104 of a patient. In some examples, target implant site 102 may include other portions of heart 100 or other locations within a body of the patient. Medical device system 100 may include a delivery tool 106 configured to house and controllably deploy relatively compact IMD 200. In some examples, a clinician may maneuver medical device system 100 to target implant site 102. For example, with the IMD loaded therein, the clinician may guide delivery tool 106 up through the inferior vena cava IVC and into the RA. In some examples, other pathways or techniques may be used to guide delivery tool 106 into other target implant sites within the body of the patient.

Figure 2A:
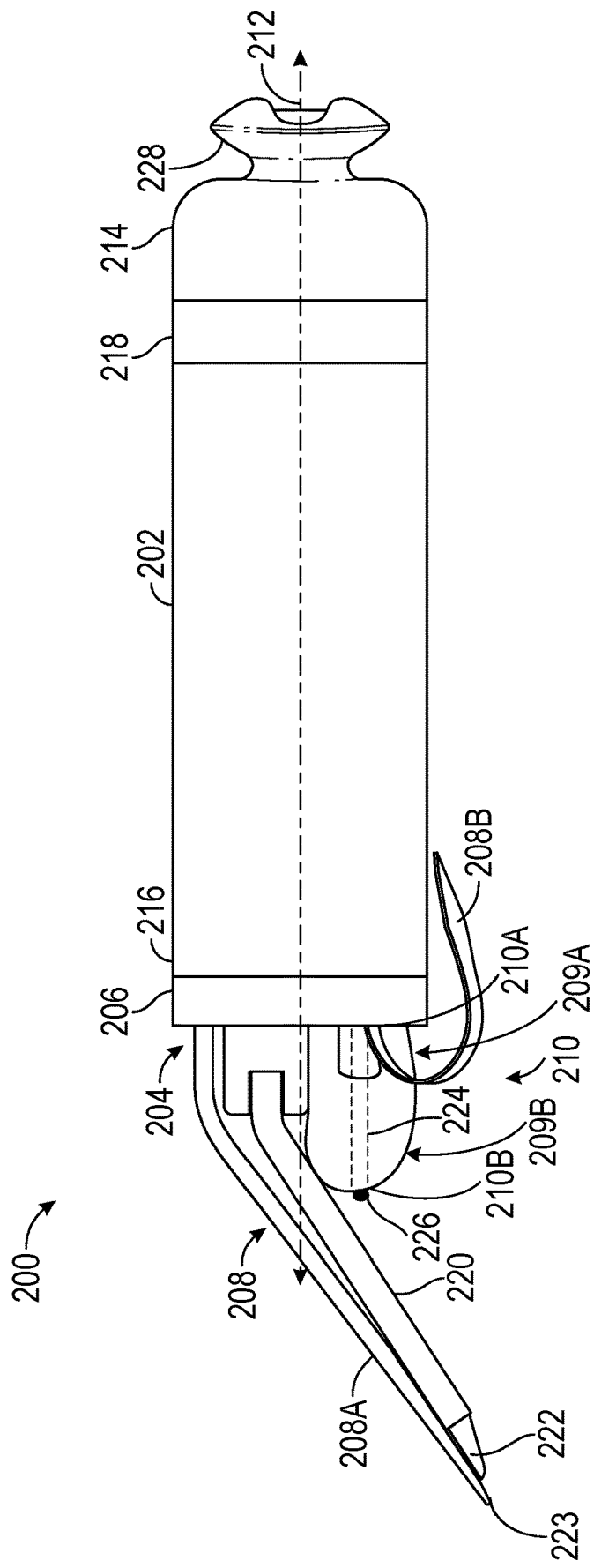
FIGS. 2A-2D are conceptual diagrams illustrating a relatively compact IMD including a fixation component.

FIG. 2A is a conceptual diagram illustrating a plan view of a relatively compact IMD 200 including a body 202, a fixation component 204 with a base 206 and one or more tines 208, and an EIA 210. Body 202 extends along longitudinal axis 212 from a proximal portion 214 to a distal portion 216. Body 202 may be formed from a biocompatible and biostable metal such as titanium. In some examples, body 202 may include a hermetically sealed body. Body 202 may include a nonconductive coating and define a return electrode 218 as an uncoated portion of body 202. IMD 200 may include any suitable dimensions. In some examples, an outer diameter of IMD 200 (e.g., outer diameter of body 202) may be between about 10 French (Fr) and about 30 Fr, such as about 20 Fr.

As discussed above, fixation component 204 may include base 206 and one or more tines 208. Base 206 may have a proximal end and a distal end aligned along a longitudinal axis, which may or may not be the longitudinal axis of body 202. The proximal end of base 206 may be attached to the distal portion of body 202.

One or more tines 208 may extend from base 206. For example, as illustrated in FIG. 2A, a penetrator tine 208A may extend from base 206. Penetrator tine 208A is configured to penetrate a tissue to fix IMD 200 to the tissue. Penetrator tine 208A may be configured to hold one or more leadlets in contact with tissue at a target implant site, e.g., target implant site 102.

In addition to penetrator tine 208A, fixation component 204 may include one or more other tines 208, such as a support tine 208B. Tines 208 may include one or more sections. For example, tines 208 may include an elastically deformable material preset into one or more curved sections and one or more optional substantially straight sections. In some examples, penetrator tine 208A and/or other tines may include one of a plurality of preset curvatures. In other examples, tines 208 may define a ribbon shape configured to deform along a plane normal to longitudinal axis 212 and resist twisting outside of the plane. In some examples, tines 208 may include two or more curved sections (e.g., knuckles) as described in U.S. Patent Application Publication No. 2020/0306522, entitled "FIXATION COMPONENTS FOR IMPLANTABLE MEDICAL DEVICES," the entire contents of which are incorporated herein by reference. For example, support tine 208B may be the same or substantially similar to tines described in U.S. Patent Application Publication No. 2020/0306522.

Tines 208 may be configured to have a target deflection stiffness and a target deployment stiffness. The target deflection stiffness may include a measure of a resistance to force applied to IMD 200 in a proximal direction when fixation component 204 is engaged with tissue at target site 102. In some examples, the target deflection stiffness may be selected to enable tines 208 to deflect a predetermined amount to enable visualization of tines 208 under fluoroscopy. In some examples, the target deflection stiffness may be within a range from about 0.2 Newtons (N) to about 0.8 N, such as about 0.3 N to about 0.6 N. The deployment stiffness may include a measure of a force applied by tines 208 as tines 208 move from a deformed configuration to an undeformed configuration upon deployment of fixation component 204 from distal opening 108 of delivery tool 106 (FIG. 1) such that the free distal end of tines 208 penetrates pectinate muscle (PM). In some examples, the target deployment stiffness may be within a range from about 0.6 N to about 1.2 N.

As illustrated in FIG. 2A, IMD 200 may include EIA 210 having proximal section 209A that defines a proximal end 210A and a distal section 209B that defines a non-incisive distal end 210B. EIA 210 may be configured to control the depth of tissue penetration of penetrator tine 208A. For example, EIA 210 may be formed such that EIA 210 contacts the tissue at a selected depth of tissue penetration of the penetrator tine. A shape of at least the non-incisive distal end 210B of EIA 210 may be bulbous, polygonal, prismatic, or any other geometry with a face that may be used as a non-incisive distal end to contact tissue. Additionally, the size of EIA 210 may be such that EIA 210 is configured to achieve a selected distance between the incisive distal end 223 of penetrator tine 208A and non-incisive distal end 210B of EIA 210, thereby controlling the depth of tissue penetration of penetrator tine 208A. Similarly, EIA 210 may be positioned on IMD 200 to achieve the selected distance between the incisive distal section of penetrator tine 208A and non-incisive distal end 210B. In any case, EIA 210 may be configured to control the depth of tissue penetration of penetrator tine 208A by contacting the tissue and resisting further penetration by penetrator tine 208A.

IMD 200 may contain electronic circuitry, including one or more of sensing circuitry (e.g., for sensing cardiac signals), therapy delivery circuitry (e.g., for generating cardiac pacing pulses), and processing circuitry for controlling the functionality of IMD 200, and may include a first leadlet 220. First leadlet 220 may terminate in a first electrode 222. For example, first leadlet 220 may include a conductor, such as an electrically conductive material, extending through a non-conductive jacket, such as polytetrafluoroethylene (PTFE) coating or polyether ether ketone (PEEK) tube, a portion of the conductor being exposed at first electrode 222. To avoid altering the properties of one or more tines 208 (e.g., penetrator tine 208A) made of a material (e.g., nitinol) that can be affected by electricity, the non-conductive jacket may extend past the one or more tines 208. The electronic circuitry may be configured to generate and deliver an electrical pulse therapy to tissue proximate to first leadlet 220 via first electrode 222, through the tissue to return electrode 218. First leadlet 220 may be spaced apart from distal portion 216 of body 202, for example, being coupled to the sensing and therapy delivery circuitry by the conductor of a hermetic feedthrough assembly (not shown in FIG. 2A).

IMD may also include a second leadlet 224 (not shown in FIG. 2A). Second leadlet 224 may extend from the proximal section of EIA 210 to the distal section of EIA 210. Second leadlet 224 may terminate in a second electrode 226 (illustrated in FIG. 3). Second leadlet 224 may be similar to first leadlet 220 in at least some aspects. For example, second leadlet 224 may include a conductor, such as an electrically conductive material, extending through a non-conductive jacket, such as PTFE coating or a PEEK tube, a portion of the conductor being exposed at second electrode 226. First leadlet 220 may function in conjunction with second leadlet 224 for bipolar pacing and sensing, and/or first leadlet 220 and second leadlet 224 may each separately function with return electrode 218 for unipolar pacing and sensing of different selected tissues. In some examples, body 202 may be overlaid with an insulative layer, for example, medical grade polyurethane, parylene, or silicone. In some examples, the insulative layer may define return electrode 218 and/or second electrode 226, for example, by removing a portion of the insulative layer to expose the metallic surface of body 202. Second electrode 226 may be used with first leadlet 220 and/or second leadlet 216 for unipolar pacing and/or sensing.

In some examples, IMD 200 may include a retrieval structure 228 fixedly attached to proximal end 214 of body 202. Retrieval structure 228 may be configured for temporarily tethering IMD 200 to a delivery catheter or a retrieval catheter, such as delivery tool 106. In some examples, retrieval structure 228 may be configured to couple to tether assemblies, such as those described in U.S. Patent Application Publication No. 2020/0353242, entitled "TETHER ASSEMBLIES FOR MEDICAL DEVICE DELIVERY SYSTEMS," the entire contents of which are incorporated herein by reference.

Figure 2B:
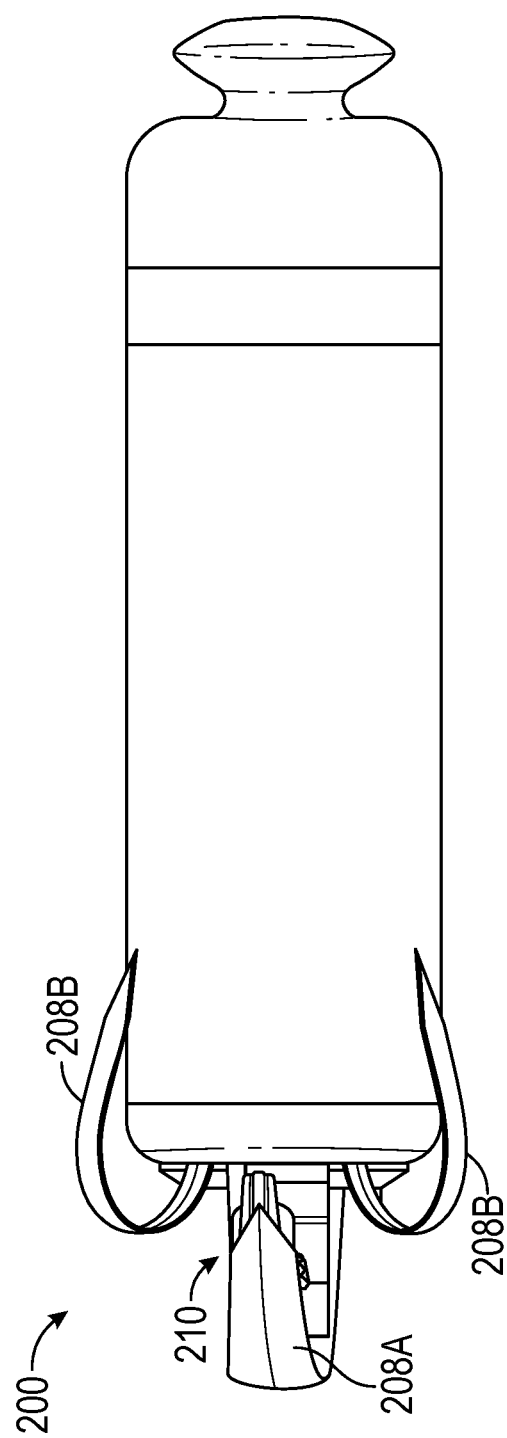
Figure 2D:
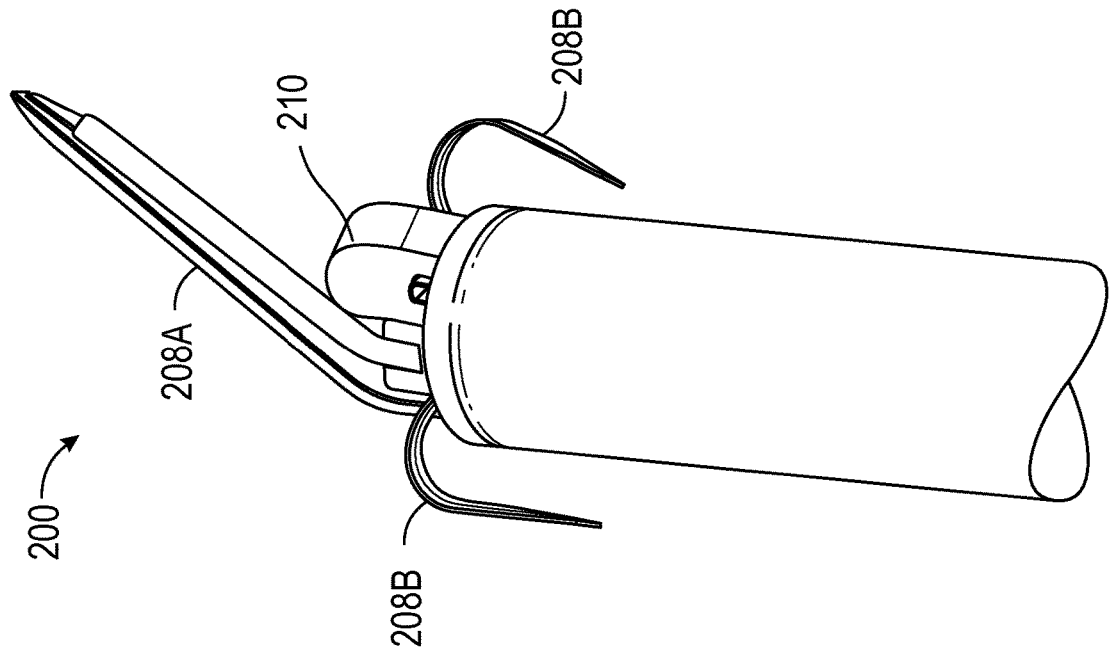
Figure 2C:
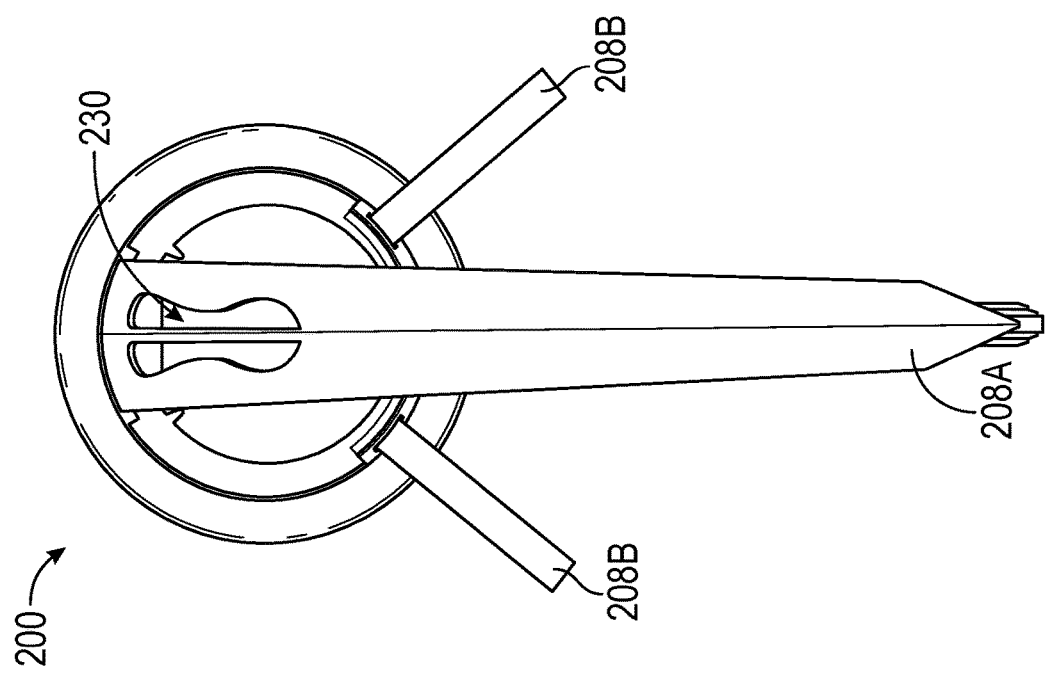

FIGS. 2B-2D also illustrate different views of IMD 200. In some examples, as illustrated in FIG. 2D, penetrator tine 208A may define an aperture 230. Aperture 230 may be configured to control a deployment stiffness or deflection stiffness of penetrator tine 208A. For example, aperture 230 may define a shear stress reduction region configured to reduce shear stress in penetrator tine 208A when bent, such as when bent into the deformed configuration or during a pull test or tug test. In some examples, at least a portion of first leadlet 220 may extend though aperture 230. By extending through aperture 230, first leadlet 220 may be adjustable. For example, a delivery catheter member may be configured to, before or after deployment of IMD 200, grasp the portion of first leadlet 220 extending through aperture 230. After deployment of IMD 200, the delivery catheter may be used to adjust an amount of the portion of first leadlet 220 extending through aperture 230 to control an amount of leadlet 220 extending beyond an incisive distal end 223 of penetrator tine 208A. In some examples, penetrator tine 208A may include other features configured to control a deployment stiffness or deflection stiffness of penetrator tine 208A or interact with other components of IMD 200. For example, penetrator tine 208A may define additional apertures or one or more grooves configured to control a deployment stiffness or deflection stiffness of penetrator tine 208A or in which first leadlet 220 may move in sliding engagement during deployment.

Figure 3:
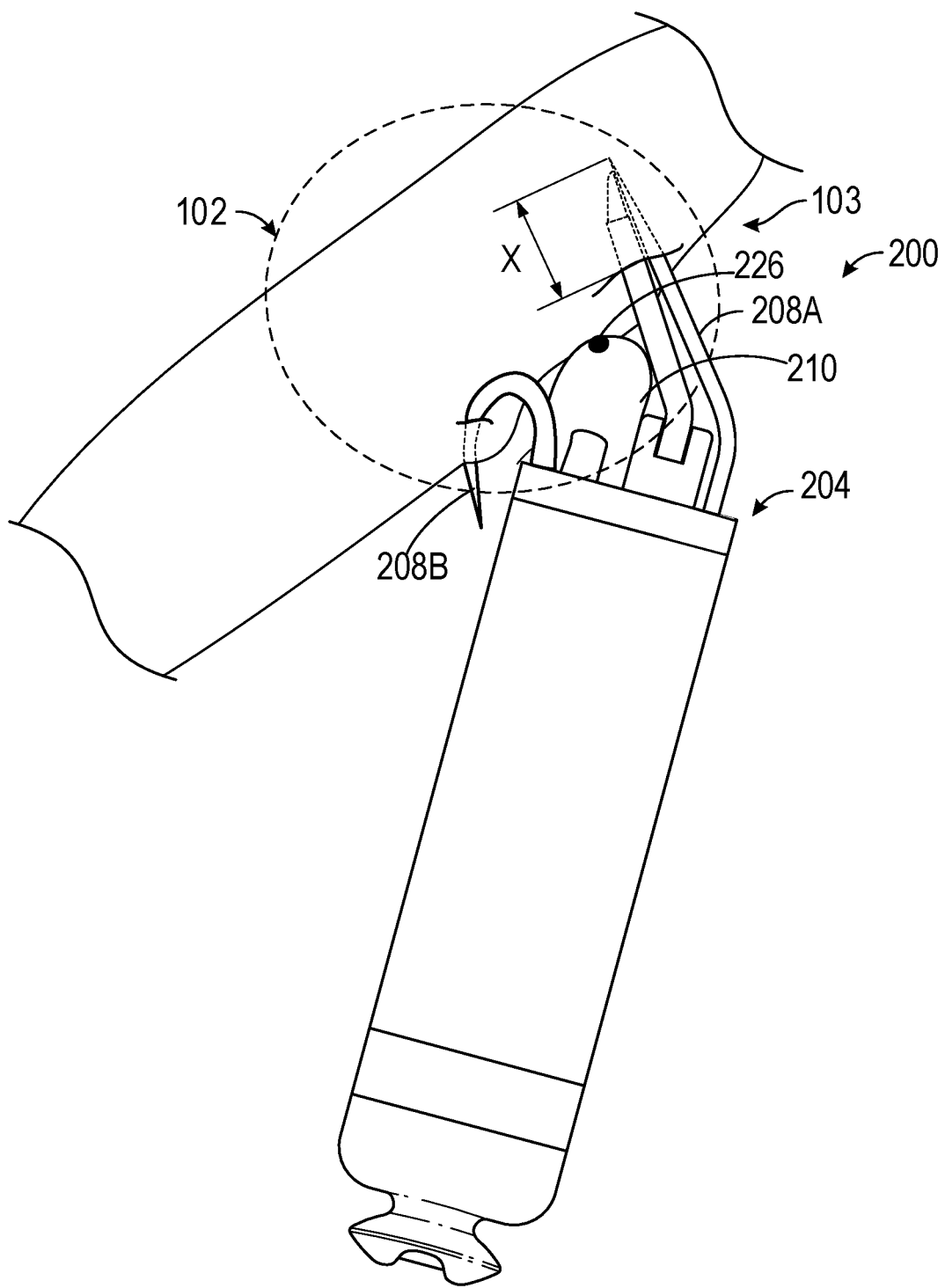
FIG. 3 is a conceptual diagram illustrating the example IMD illustrated in FIGS. 2A-2D implanted at an example target implant site.

FIG. 3 is a conceptual diagram illustrating IMD 200 implanted at target implant site 102. Tines 208 may define a deformable preset curvature configured to position leadlets 208 and 216 at selected tissue of a target implant site 102. Target implant site 102 includes a portion the right atrial RA wall, such as the atrioventricular septum having an atrial surface 103 and a ventricular surface 105. In some examples, the target implant site may include other locations inside the heart, such as at least one of an interatrial septum or an interventricular septum. In other examples, target implant site 102 may include other tissues within a body of a patient. When deployed at target implant site 102, tines 208 may have a deployment stiffness that enables a respective tine 208 (e.g., penetrator tine 208A, support tine 208B, etc.) to penetrate selected tissue at target implant site 102. For example, IMD 200 may be secured at target implant site 102 by tines 208 of fixation component 204 penetrating through the myocardium, such as a layer of pectinate muscle. Tines 208 may be configured for spring-loaded release upon deployment out through distal opening 108 of delivery tool 106 (FIG. 1), such that free distal end of tines 202 (e.g., free distal end 223 of penetrator tine 208A) penetrates the myocardium. It should be noted that alternate suitable implant sites for fixation component 204 can be along any suitable surface of the heart or other tissue within a body of a patient. By controlling the deployment stiffness, tines 208 may have improved tissue fixation, including control of a depth of penetration and an amount of tissue engagement in a lateral direction.

EIA 210 may operate in conjunction with tines 208. For example, EIA 210 may be configured to control a depth X of tissue penetration of penetrator tine 208A. Depth X may include the distance between the incisive distal tip of penetrator tine 208A and the distal end of EIA 210, and/or a length of the distal section of penetrator tine 208A that penetrates the tissue. In some examples, depth X of tissue penetration of penetrator tine 208A may be within a range from about 1 millimeter (mm) to about 20 mm, such as within a range from about 4 mm to about 10 mm. EIA 210 may control a depth of tissue penetration by contacting the tissue and resisting further penetration by penetrator tine 208A. In such an example, may be within a range from about 4 millimeters to about 10 millimeters.

IMD 200 may be implanted at target implant site 102 such that first electrode 222 and second electrode 226 are in contact with the selected tissue. When positioned in such a manner, first electrode 226 of first leadlet 220 and second electrode of second leadlet 224 may function in conjunction for bipolar pacing and sensing, and/or first electrode 222 and second electrode 226 may each separately function with return electrode 218 for unipolar pacing and sensing of different selected tissues.

Figure 4:
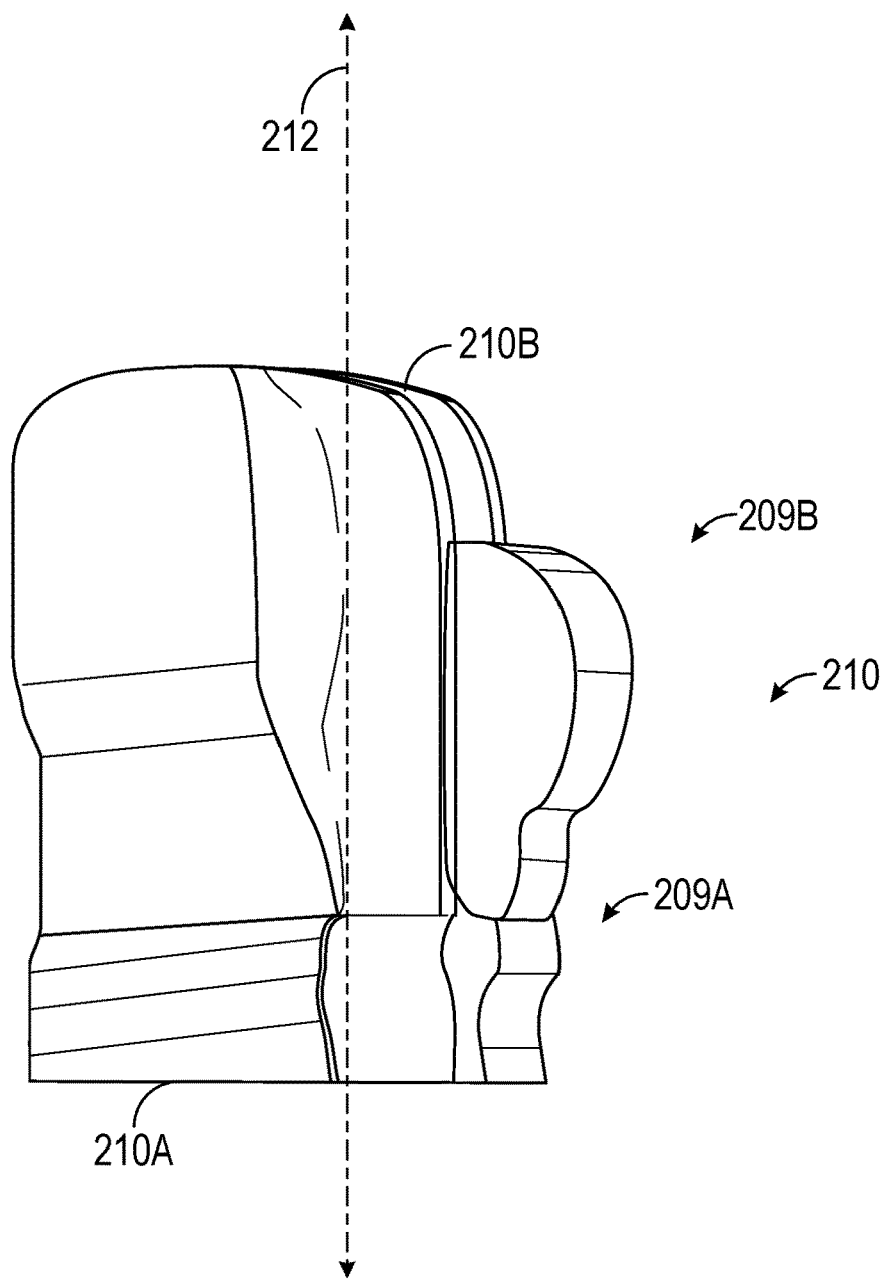
FIG. 4 is a conceptual diagram illustrating an electrode interface assembly.

FIG. 4 is a conceptual diagram of an example EIA 210. EIA 210 may include a proximal section 209A defining proximal end 210A and a distal section 209B defining distal end 210B. Proximal end 210A may be attached to and extend distally from the distal portion of body 202 along longitudinal axis 212. Distal end 210B may extend from proximal section 209A and define a non-incisive distal end 210B. Distal end 210B may be configured to contact the tissue to control a depth of tissue penetration of the penetrator tine 208A. For example, EIA 210 may be formed such that the length between proximal end 210A and non-incisive distal end 210B results in a distance between the incisive distal section of penetrator tine 208A and non-incisive distal end 210B of EIA 210 within a range from about 4 millimeters to about 10 millimeters. Non-incisive distal end 210B of EIA 210 may be bulbous, polygonal, prismatic, or any other geometry with a face that may be used as a non-incisive distal end to contact tissue.

During deployment of IMD 200, EIA 210 may apply a force to first leadlet 220, thus urging first leadlet 210 toward penetrator tine 208A and guiding first leadlet 222 into the puncture at target implant site 102. As fixation component 204 is further deployed, penetrator tine 208A may return from a deformed (e.g., pre-deployment) configuration to (or at least towards) the undeformed (e.g., deployed) configuration. Upon reaching a selected depth of tissue penetration of penetrator tine 208A, EIA 210 may contact the tissue to resist further tissue penetration.

EIA 210 may include second electrode 226. For example, EIA 210 may define a passage through which second leadlet 224 may extend from proximal end 210A to non-incisive distal end 210B. Second leadlet 224 may terminate at second electrode 226. When EIA 210 contacts the tissue to resist further tissue penetration, second electrode 226 may also contact the tissue, such that second electrode 226 may function for pacing and/or sensing.

Figure 5A:
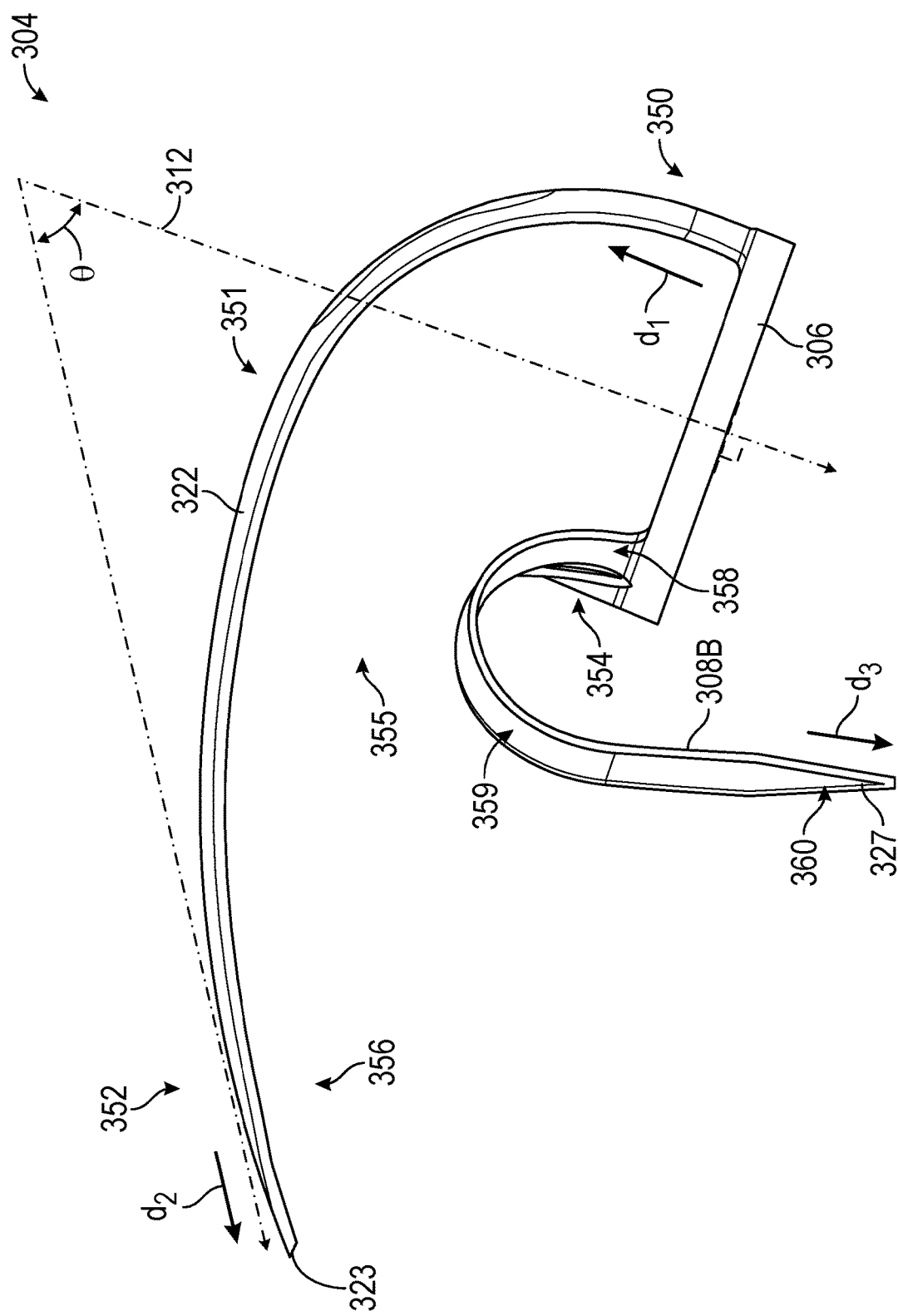
FIGS. 5A and 5B are conceptual diagrams illustrating an example fixation component.
Figure 5B:
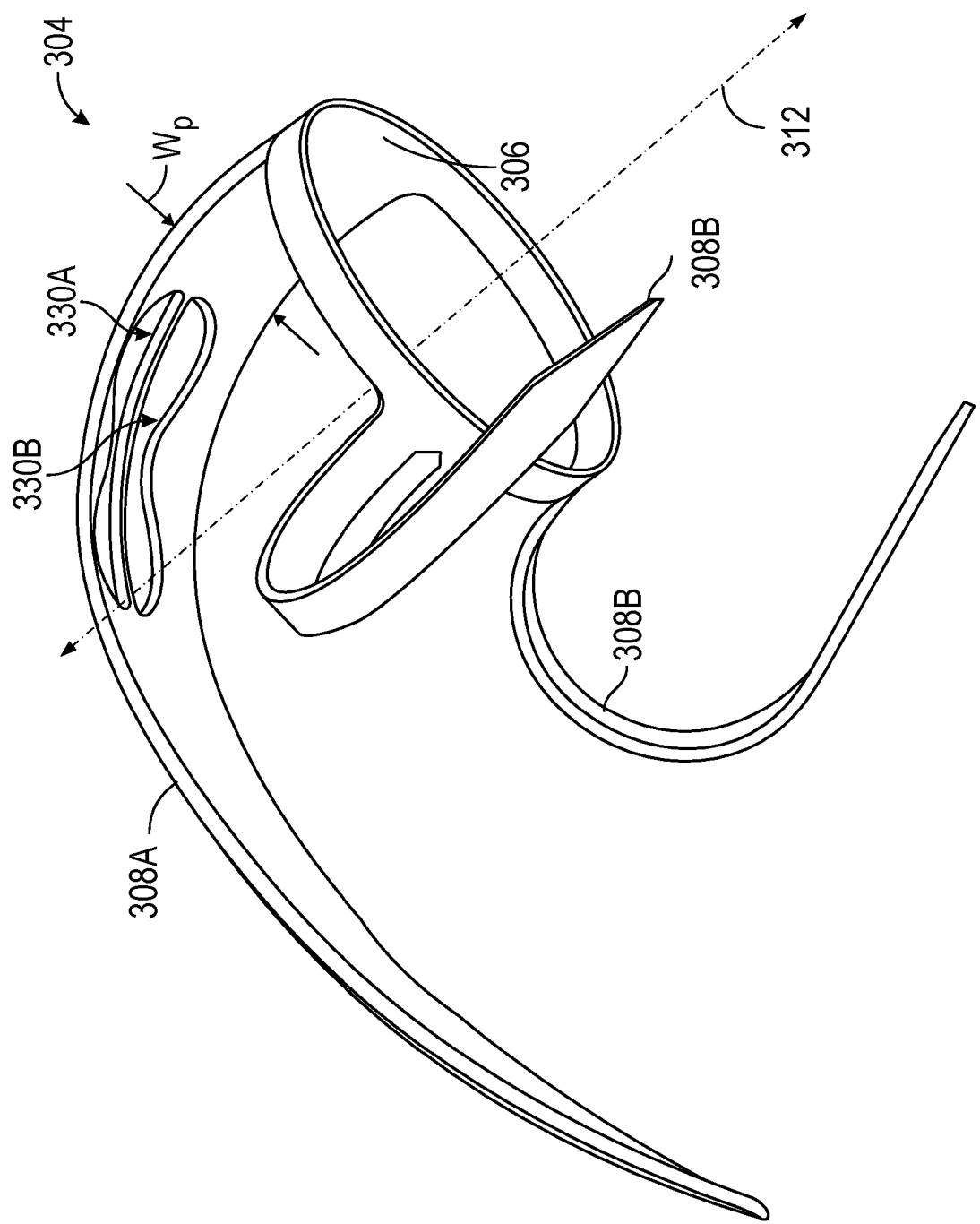

FIGS. 5A and 5B are conceptual diagrams illustrating an example fixation component 304. Fixation component 304 may be the same as or substantially similar to fixation component 204, except for the differences described herein. For example, fixation component 304 may include a penetrator tine 308A and may optionally include additional tines 308 (e.g., a support tine 308B). Tines 308 are illustrated in a deployed (e.g., undeformed) configuration.

As illustrated in FIGS. 5A and 5B, fixation component 304 may include base 306. Base 306 may define a longitudinal axis 312 of fixation component 304. Base 306 may be mounted around distal portion 216 of body 202 such that a perimeter of fixation component 304 extends around body 202, and longitudinal axis 312 may be generally aligned along longitudinal axis 212 of IMD 200 (FIG. 2A).

As illustrated in FIG. 5A, penetrator tine 308A may include proximal section 350, curved section 351, and distal section 352. Each of proximal section 350, curved section 351, and distal section 352 may include any suitable length. In some examples, a length of penetrator tine 308A may be within a range from about 2 mm to about 15 mm, such as from about 4 mm to about 10 mm. Proximal section 350 is fixedly attached to base 306. Proximal section 350 extends in a first direction $d_1$. In some examples, first direction $d_1$ may be substantially parallel to longitudinal axis 312. In some examples, first direction $d_1$ may be at an angle relative to longitudinal axis 312, such as for example, between about 0 degrees to about 5 degrees. Curved section 351 may include a deformable preset curvature. Curved section 351 extends from proximal section 350 laterally across longitudinal axis 312 to distal section 352. In some examples, curved section 351 may include a single radius within a range from about 0.06 inch (1.524 mm) to about 0.08 inch (2.032 mm), such as about 0.067 inch±0.010 inch (1.7018 mm±0.254 mm). In some examples, curved section 351 may include more than one curved section.

Distal section 352 may include a substantially straight segment that terminates in distal end 323. Distal end 323 of penetrator tine 308A may include an incisive shape. In some examples, the incisive shape may include a shape tapering to a point or an edge that is sufficiently small to pierce a tissue or cut a tissue. In some examples, an incisive shape may include a pointed shape, such as a needle shape. In some examples, an incisive shape may include a blade shape that tapers to a sharp edge, a tanto tip, a forked tip, a dual tanto forked tip, or a dual tanto forked tip with curved cutting surface. In some examples, the shape of distal end 323 of penetrator tine 308A may be based, at least in part, on a deployment force of penetrator tine 308A. For example, penetrator tine 308A having a lesser deployment force may require a sharper distal end 323 to achieve penetration of a tissue, compared to a penetrator tine 308A having a greater deployment force which may have a relatively less sharp distal end 323 to achieve penetration of a tissue. In this way, the selected shape of the distal end 323 of penetrator tine 308A may improve tissue penetration, reduce a deployment force required to penetrate tissue, and/or better control tissue penetration depth compared to other distal ends.

Distal section 352 may be oriented by curved section 351 such that distal section 352 substantially extends, within manufacturing limits, in direction $d_2$. In some examples, the angle θ between $d_1$ and $d_2$ may be within a range between about 35 degrees and 145 degrees relative to longitudinal axis 312, such as about 90 degree or about 135 degrees.

Support tine 308B may include proximal section 358, curved section 359, and distal section 360. Each of proximal section 358, curved section 359, and distal section 360 may include any suitable length. Proximal section 358 is fixedly attached to base 306. Proximal section 358 extends in a first direction $d_1$, as discussed above. Curved section 359 may include a deformable preset curvature. Curved section 359 extends from proximal section 358 laterally, outward from longitudinal axis 312 to distal section 360. In some examples, curved section 355 may include a single radius within a range from about 0.06 inch (1.524 mm) to about 0.08 inch (2.032 mm), such as about 0.067 inch±0.010 inch (1.7018 mm±0.254 mm). In some examples, curved section 355 may include more than one curved section. Distal section 360 may include a substantially straight segment that terminates in distal end 327. Distal end 327 of support tine 308B may include any suitable shape, such as, for example, a rounded shape or an incisive shape. Distal section 360 may be oriented by curved section 359 such that distal section 360 substantially extends, within manufacturing limits, in direction $d_3$.

The shape (e.g., deformable preset curve) and width of each tine of tines 308, and, in some examples, the super-elastic stiffness properties of nickel-titanium alloy, may provide a sufficient spring force and structural stiffness for tines 308 to engage tissue for the fixation of IMD 200 at an implant site when deployed by delivery tool 106, as described in greater detail below. For example, with reference to FIG. 5B, penetrator tine 308A may have a proximal width "$W_P$" in a range from about 0.020 inch (0.508 mm) to about 0.1 inch (2.54 mm), such as about 0.06 inch (1.524 mm). In some examples, tines 308 may have a substantially constant width (e.g., constant or nearly constant within the limits of common manufacturing tolerances) along the length of tines 308. For example, proximal section 358, curved section 359, and distal section 360 of support tine 308B may have a substantially constant width. In some examples, a width of tines 308 may taper toward a respective distal end. For example, a width of penetrator tine 308A may taper from about 0.1 inch (2.54 mm) at a proximal width $W_P$ to about 0.024 inch (0.6 mm) at a distal width. In some examples, the taper of penetrator tine 308A may be selected and shaped to provide tissue penetration up to a selected width of the taper. For example, penetrator tine 308A may taper from about 0.59 inch (1.5 mm) at a proximal width $W_P$ to about 0.020 inch (0.508 mm) at a distal width and be configured to penetrate tissue up to about a width of 0.028 inch (0.7 mm). In some examples, a tapered portion of a respective tine of tines 308 may include a plurality of tapers, each taper having a respective maximum width and respective minimum width. Generally, a tapered portion may increase the flexibility of a respective tine relative to an untampered portion. In this way, one or more tapers may be used to selectively control a deployment stiffness, a deflection stiffness, and/or a tissue penetration depth. In some examples, a width of tines 208 may be selected to provide a radiopaque density that facilitates fluoroscopic visualization during and after the implant procedure.

In some examples, rather than tapered portions, tines 308 may include cutouts, engravings, embossing, or other variations in the thickness of tines 308. For example, penetrator tine 308A may include apertures 336A and 336B. Apertures 336A and 336B may include any suitable shape, length, and/or width. Similarly, 308B may include aperture 338. In some examples, cutouts, engravings, embossing, or other variations in the thickness of penetrator tine 308 may be configured to increase the flexibility of a selected portion of penetrator tine 308 relative to other portions of penetrator tine 308. For example, apertures 336A and 336B may increase a flexibility of curved section 351 of penetrator tine 308A. By increasing the flexibility of the selected portion of a respective tine of penetrator tine 308, the respective tine may have, after forming the preset curvature, a reduced deployment stiffness and/or deflection stiffness compared to a tine without cutouts, engravings, embossing, or other variations in the thickness.

As illustrated in FIG. 5B, tines 308 may be spaced apart from one another around a perimeter of base 306. Base 306 may have any suitable inner diameter and outer diameter. In some examples, base 306 may have an inner diameter within a range from about 0.1 inch (2.54 millimeters, mm) to about 0.3 inch (7.62 mm), such as 0.20 inch (5.08 mm), and an outer diameter within a range from about 0.11 inch (2.794 mm) to about 0.31 inch (7.874 mm), such as about 0.21 inch (5.334 mm). In some examples, fixation component 304 may be mounted to distal end 216 of device body 202, for example, in a manner that is the same or substantially similar to that described in U.S. Pat. No. 10,099,050B2 (filed on Jan. 19, 2017), which is incorporated herein by reference in its entirety. In some examples, fixation component 304 may include separately formed tines 308 that are individually mounted to distal end 216 of device body 202 (e.g., not integrated together with base 306).

Tines 308 may include any suitable elastically deformable biocompatible material. In some examples, tines 308 may include a super-elastic material, such as, for example, a nickel-titanium alloy. For example, fixation component 304 may be cut from a medical grade nickel-titanium alloy tubing that conforms to the chemical, physical, mechanical, and metallurgical requirements of the ASTM F2063 standard, and has a wall thickness of about 0.005 inch (0.127 mm). In this way, tines 308 may be integrally formed with base 306 and each tine of tines 308 may have a constant thickness "t" of about 0.005 inch±0.001 inch (0.127 mm±0.0254 mm). In some examples, after cutting the tubing or otherwise forming fixation component 304, tines 308 may be shaped into a preset configuration by bending and holding tines 308, while heat treating according to methods known to those skilled in the art.

In some examples, the tines of a fixation component may include more than two curved sections to result in a target deflection stiffness and a target deployment stiffness.

Figure 6A:
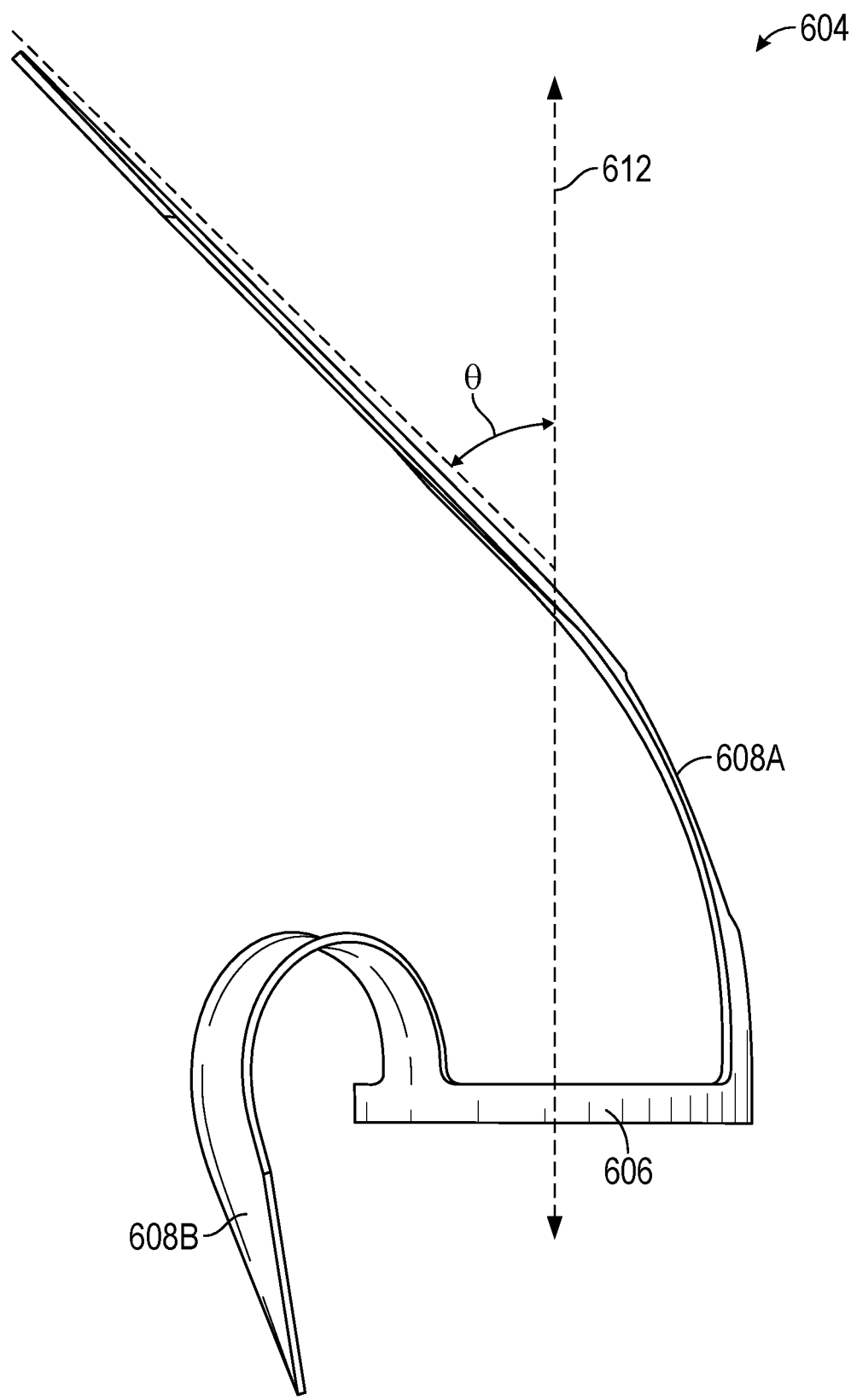
FIGS. 6A-6C are conceptual diagrams illustrating an example fixation component that includes a having a plurality of curved sections.
Figure 6B:
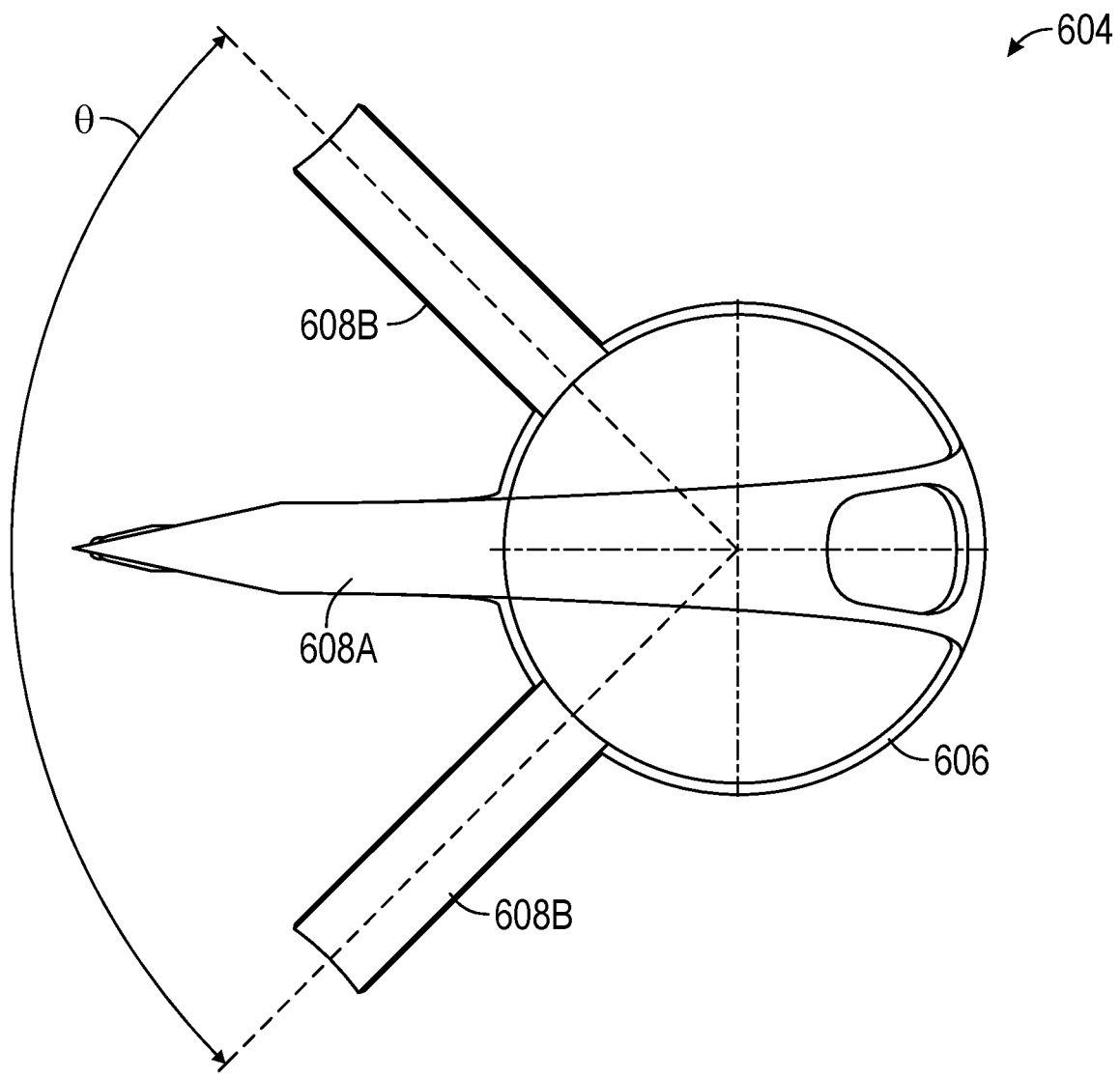
Figure 6C:
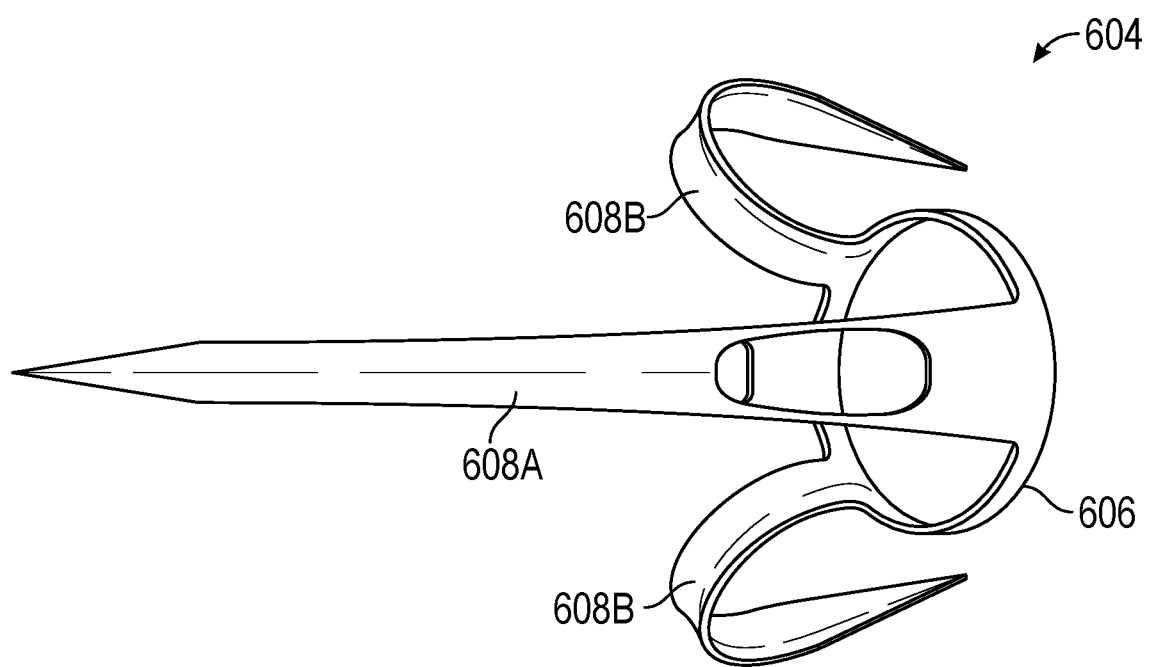

FIGS. 6A-6C are conceptual diagrams illustrating an example fixation component 604 that includes a 608B having a plurality of curved sections. Fixation component 604 may be the same as or substantially similar to fixation components 202 and/or 302 discussed above in reference to FIGS. 2A-5B, except for the differences describe herein. For example, fixation component 604 includes base 606 from which tines 608 and are spaced apart from one another around a perimeter of base 606. Base 606 may define a longitudinal axis 612 of fixation component 604, which may, in some examples, generally aligned along longitudinal axis 212 of IMD 200 (FIG. 2A). Penetrator tine 608A and 608B extend laterally, outward from longitudinal axis 612 at an angle θ of about 45 degrees.

As illustrated in FIG. 6B, tines 608 are spaced apart from one another around a perimeter of base 606. In some examples, support tines 608B may be spaced apart relative to one another at any suitable angle 1, such as an angle within a range from about 60 degrees to 120 degrees, such as 90 degrees. In some examples, a spacing of support tines 608B about 135 degrees from penetrator tine 608A, e.g., 90 degrees relative to another support tine, may improve fixation of an IMD (e.g., IMD 200) by increasing an amount of tissue engaged by support tines 608B if penetrator tine 608A is off-perpendicular relative to a selected tissue at a target implant site.

Figure 7B:
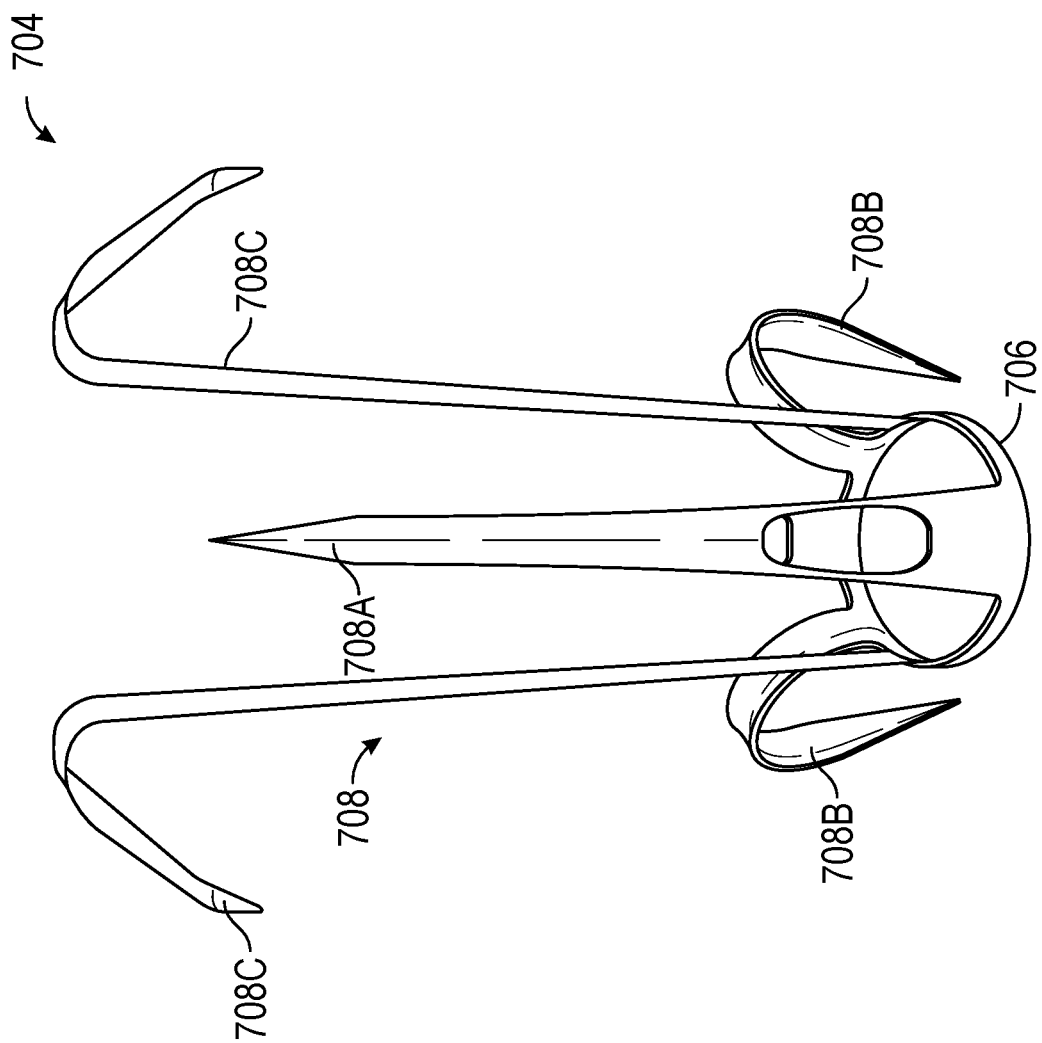
FIGS. 7A and 7B are conceptual diagrams illustrating an example fixation component that includes guiding tines.
Figure 7A:
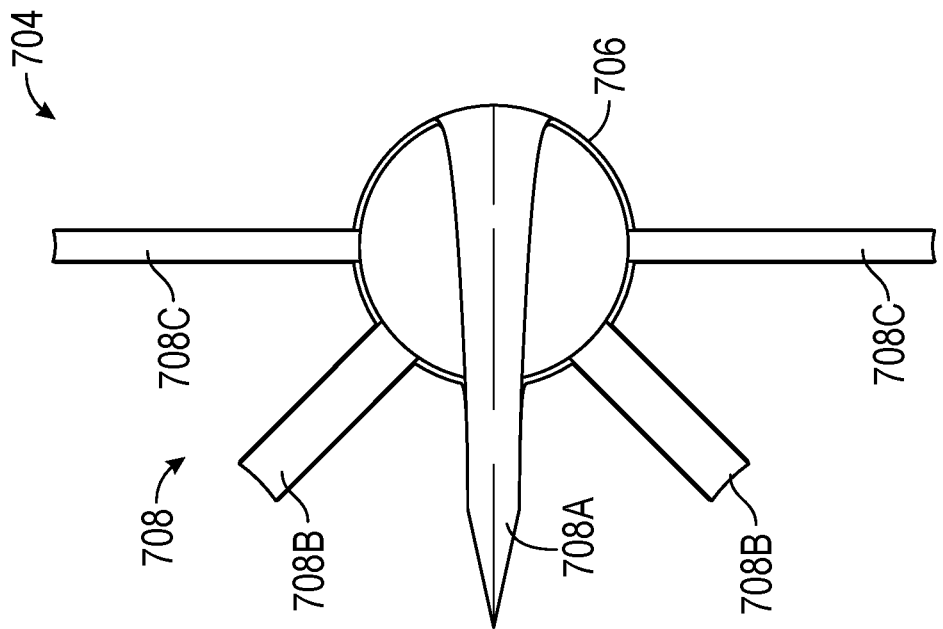

In some examples, a fixation component may include one or more guiding tines. FIGS. 7A and 7B are conceptual diagrams illustrating an example fixation component 704 that includes guiding tines 708C. Fixation component 704 may be the same as or substantially similar to fixation components 204, 304, and/or 604 discussed above in reference to FIGS. 2A-6C, except for the differences describe herein. For example, fixation component 704 includes base 706 from which tines 708 extend. Tines 708 include penetrator tine 708A, support tines 708B, and guiding tines 708C. Guiding tines 708C may be spaced apart from penetrator tine 708A at an angle within a range from about 80 degrees to about 90 degrees. In some examples, guiding tines 708C may include non-incisive distal ends. In some examples, guiding tines 708C may be used to determine and/or control an orientation of an IMD (e.g., IMD 200) during deployment. For example, guiding tines 708C may have a length greater than the other tines, e.g., penetrator tine 708A. During deployment, guiding tines 708C may extend out of a distal opening of a delivery catheter before the other tines. In this way, a clinician may partially deploy IMD 200 to provide a clinician with a visual indication, e.g., via fluoroscopy, of the orientation of IMD 200 prior to deployment of penetrator tine 708A and/or support tines 708B. In some examples, guiding tines 708C may contact selected tissue at the target implant site prior to deployment of penetrator tine 708A. By contacting selected tissue at the target implant site prior to deployment of penetrator tine 708A guiding tines 708C may orient an IMD such that penetrator tine 708A is approximately perpendicular to the selected tissue.

Figure 8B:
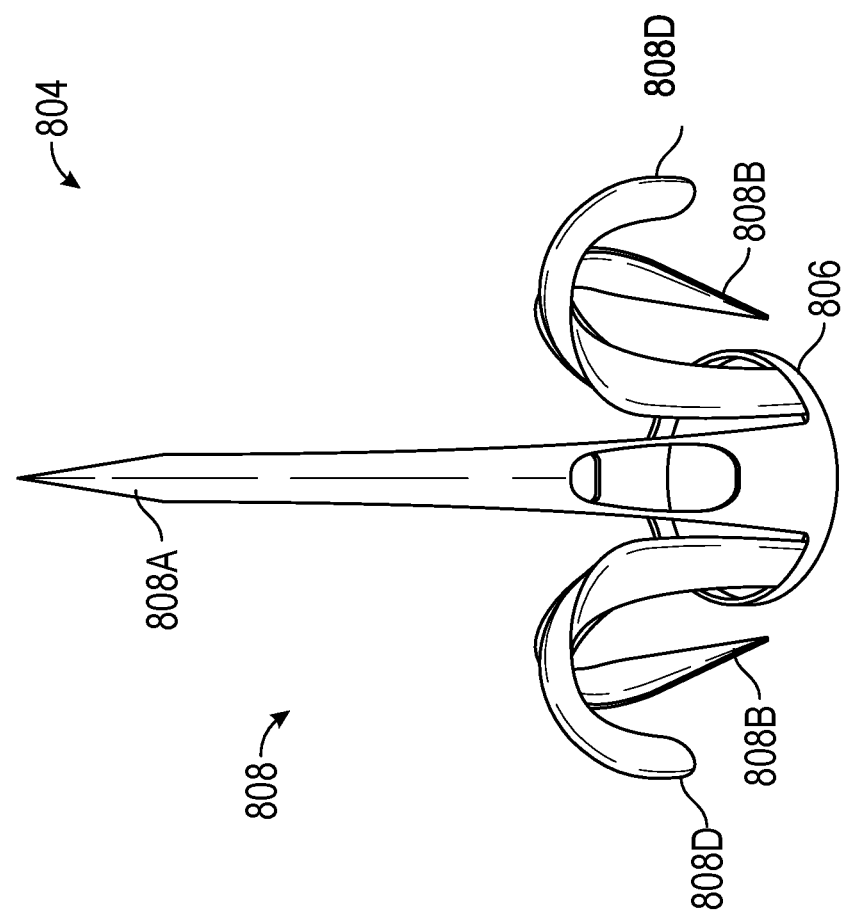
FIGS. 8A and 8B are conceptual diagrams illustrating an example fixation component that includes deployment tines.
Figure 8A:
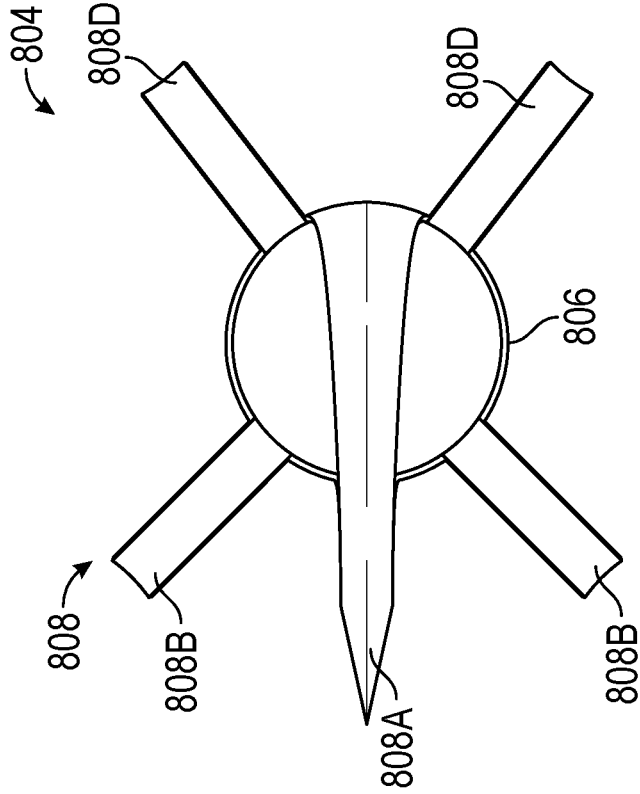

In some examples, a fixation component may include one of more deployment tines. FIGS. 8A and 8B are conceptual diagrams illustrating an example fixation component 804 that includes deployment tines 808D. Fixation component 802 may be the same as or substantially similar to fixation components 204, 304, 604, and/or 704 discussed above in reference to FIGS. 2A-7B, except for the differences describe herein. For example, fixation component 804 may include base 806 from which tines 808 extend. Tines 808 include penetrator tine 808A, support tines 808B, and deployment tines 808D. Deployment tines 808D may be spaced apart from penetrator tine 708A at an angle within a range from about 10 degrees to about 45 degrees. In some examples, deployment tines 808D may include non-incisive distal ends. Deployment tines may be configured to increase a deployment force of IMD 200 to improve, for example, tissue penetration of penetrator tine 808A and/or support tines 808B during deployment. In some examples, tines may include both guiding tines (e.g., guiding tines 708C) and deployment tines 808D. In this way, deployment tines 808D may be added to fixation component 804 to achieve a selected deployment force.

Figure 9:
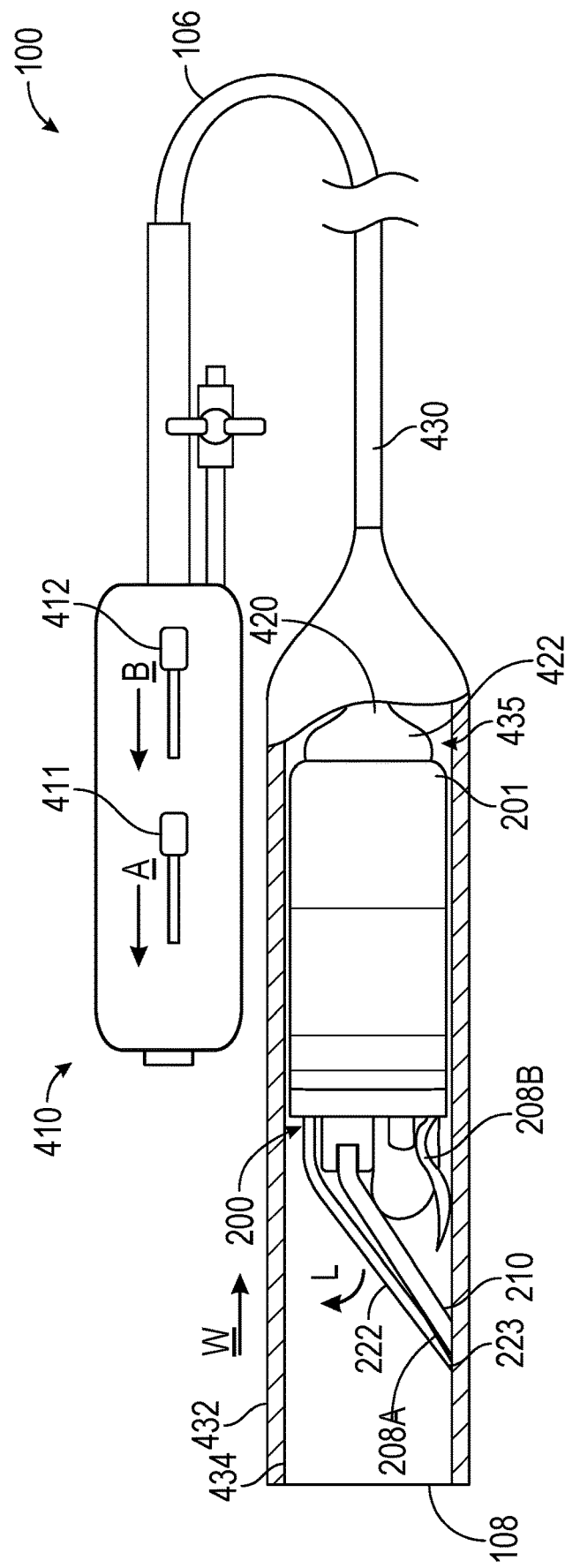
FIG. 9 is a conceptual diagram illustrating a partial cut-away section of an example medical device system including a delivery tool and an IMD.

FIG. 9 is a conceptual diagram illustrating a partial cut-away section of an example medical device system 100 including a delivery tool 106 and an IMD 200. For purposes of illustration, the distal end of delivery tool 106 is enlarged relative to handle 410. Additionally, although medical device system 100 is described in reference to fixation component 204 described in reference to FIGS. 2A-3, in other examples, medical device system 100 may include other fixation components.

During use, IMD 200 may be loaded into delivery tool 106 for deployment to a target implant site (e.g. target implant site 102). Delivery tool 106 may include a handle 410, an elongate outer member 430, and an elongate inner member 420 that extends within lumen 435 of outer member 430. Inner member 420 may include a distal end 422 configured to engage IMD 200 by abutting proximal end 214 of body 202 (e.g., as shown in the cut-away section). An entirety of IMD 200 may be loaded within tubular sidewall 432 that defines a distal portion of outer member lumen 430, for example, having been loaded therein by pulling IMD 200, with body proximal end 214 leading, in through lumen distal opening 108. In some examples, an inner surface 434 of tubular sidewall 432 may engage tines 208 of fixation component 204 as IMD 200 is loaded into lumen 435 to deform tines 208 (per arrow L) and then to hold each tine of tines 208 of the loaded IMD 200 in a deformed configuration, e.g., a spring-loaded configuration.

Handle 410 may be configured to control movement of delivery tool 106 and/or deployment of IMD 200. The clinician may position medical device system 100 by advancing delivery tool 403 through vasculature of the patient, for example, from a femoral venous access site and up through the inferior vena cava IVC (FIG. 1), or a radial artery access site. Delivery tool 106 may include articulating features to facilitate the navigation of the distal portion of delivery tool 106. For example, inner member 420 of delivery tool 106 may include a pull wire assembly (not shown) integrated therein and being coupled to another control member 411 of handle 410 that, when moved per arrow A, causes inner member 420 and outer member 430 to bend along distal portions thereof.

In some examples, a proximal end of outer member 430 may be coupled to a control member 412 of handle 410 such that an entirety of outer member 430 is movable with respect to inner member 420, via control member 412. For example, after positioning medical device system 100 at selected tissue in proximity to a target implant site 102 (FIG. 1), a clinician may retract outer member 430, per arrow W, relative to IMD 200 and inner member 420, thereby release the spring loading fixation component 204 to deploy IMD 200 out through distal opening 108 such that tines 208 engage with the selected tissue to secure IMD 200 at the implant site. Additionally, or alternatively, delivery tool 106 may be configured so that a clinician can advance inner member 420 relative to outer member 430 to push IMD 200 out through distal opening 108 for deployment. A length of outer member 430, between handle 410 and distal opening 108 may be between about 100 cm and about 120 cm. Suitable construction detail for a delivery tool like delivery tool 106 is described in U.S. Pat. No. 9,526,522 to Wood et al., which is incorporated herein by reference in its entirety.

Penetrator tine 208A may be configured to penetrate or cut a selected tissue to form a puncture. EIA 210 may be configured to protect first leadlet 220 during deployment. In some examples, during deployment from delivery catheter 106, penetrator tine 208A may initially penetrate selected tissue of atrial surface 103 to form a puncture. Also, EIA 210 may urge first leadlet 220 toward penetrator tine 208A, thereby guiding leadlet 220 and 220B into the puncture. For example, the shape of the non-incisive distal end of EIA 210 may be configured to urge first leadlet 220 toward penetrator tine 208A by applying a force to first leadlet 220 in the direction of penetrator tine 208A during and/or after deployment. By urging first leadlet 220 toward penetrator tine 208A, EIA 210 may reduce undesired displacement of first leadlet 220 and/or reduce mechanical damage to first leadlet 220 (e.g., as first leadlet 220 passes out of delivery catheter 106).

As fixation component 204 is further deployed, penetrator tine 208A may return from the deployed configuration, for example, as illustrated in FIG. 3. Upon the penetrator tine 208 reaching the selected depth of tissue penetration, EIA 210 may begin to contact the tissue and resist further tissue penetration. When in the deployed configuration, first leadlet 220 may extend in a distal direction between penetrator tine 208A. In this way, first leadlet 220 may extend from distal portion 216 of body 202 of IMD 200 to reach a selected target tissue, such as tissue near ventricular surface 105. In a similar fashion, second leadlet 224 may be urged against tissue at atrial surface 103 by EIA 210, and optionally penetrator tine 208A support tine 208C. In this way, IMD 200 may be configured to penetrate the atrioventricular septum to enable pacing and/or sensing at ventricular surface 105 via first electrode 222 and pacing and/or sensing at atrial surface 103 via second electrode 226.

After deployment at target implant site 102, in some examples, a deflection stiffness of tines 208 may enable a clinician to confirm adequate fixation of tines 208 into tissue of a patient. For example, a pull test or tug test may be performed under fluoroscopy to confirm that tines 208 have engaged the tissue to confirm adequacy of implantation of IMD 200. The pull test or tug test may include the clinician pulling or tugging on the deployed IMD 200 and observing movement of tines 208 to determine if tines 208 are engaged in tissue, e.g., tines 208 that are embedded in tissue deflect or bend as deployed IMD 200 is pulled or tugged. By controlling the deflection stiffness, tines 208 may have an improved flexibility that enables a clinician to more easily confirm tissue engagement.

Figure 10:
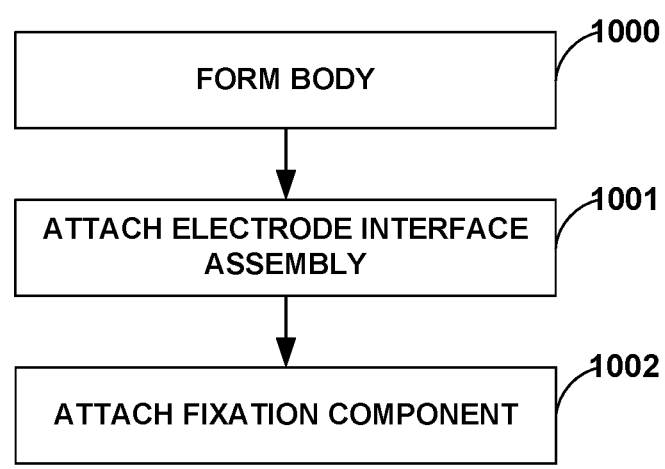
FIG. 10 is a flow diagram illustrating an example method of manufacturing an example fixation component.

IMD 200 may be manufactured using any suitable technique. FIG. 10 is a flow diagram illustrating an example method of manufacturing IMD 200. Although the technique illustrated in FIG. 10 is described in reference to IMD 200 illustrated in reference to FIGS. 2A-2D, the technique may be used to manufacture other IMDs, such as IMDs with fixation component 304, 604, 604, 704, and/or 804 described in reference to FIGS. 4A-8B, and fixation component 204 describe in reference to FIGS. 3A and 3B.

The technique illustrated in FIG. 10 may include forming body 202 extending from proximal portion 214 to distal portion 216 along longitudinal axis 212 (1000). In some examples, forming body 202 may include shaping a biocompatible and biostable metal such as titanium into a hermetically sealed body. Forming body 202 may include a pre-processing or post-processing step, such as applying a nonconductive coating and defining a return electrode 218 as an uncoated portion of body 202. In some examples, body 202 may be dimensioned so that an outer diameter of IMD 200 (e.g., outer diameter of body 202) may be between about 10 French (Fr) and about 30 Fr, such as about 20 Fr.

The technique illustrated in FIG. 10 may also include attaching EIA 210 to distal portion 216 of body 202 (1001). EIA 210 may be attached using one or more known techniques, such as an adhesive, fastener, screw, weld, and the like. EIA 210 may include proximal end 210A and non-incisive distal end 210B (1004). EIA 210 may be attached to distal portion 216 of body 202 such that proximal end 210B extends distally from distal portion 216 of body 202 along longitudinal axis 212. In some cases, EIA 210 may be integrally formed and then attached to IMD 200. For example, EIA 210 may be integrally formed from a polymer by one or more of molding, additive manufacturing such as three-dimensional printing, and/or subtractive manufacturing such as machining or etching. In some examples, EIA 210 is formed to define a channel through which second leadlet 224 may extend. In other examples, EIA may be formed to encapsulate at least a portion of second leadlet 224. For example, such that at least electrode 226 may be exposed. In any case, distal end 210B of EIA 10 may be configured to contact a tissue to control a depth of tissue penetration of penetrator tine 208A.

The technique illustrated in FIG. 10 may also include attaching fixation component 204 to body 202 of IMD 200 (1002). Fixation component 204 may be attached to body 202 using one or more known techniques, such as an adhesive, fastener, screw, weld, and the like. In some examples, fixation component 204 may be formed and then attached to body 202. For example, fixation component 204 may be formed to include base 206 and tines 208.

Forming base 206 may include forming a base having a proximal end and a distal end aligned along the longitudinal axis. The proximal end of base 206 may be attached to distal portion 216 of body 202. Forming base 206 may include cutting a tube, such as a metal tube, a nickel titanium alloy tube, or a stainless-steel tube, to define base 206. Forming base 206 may include pre-processing or post-processing steps, such as abrading, coating, heat treating, or polishing a substrate defining base 206.

Forming tines 208 may include extending tines 208 from base 206 and spacing tines 208 apart from one another. Tines 208 may include penetrator tine 208A. Penetrator tine 208A may include a proximal section attached to and extending from distal end 216 of base 202 in a first direction. Penetrator tine 208A may further include a curved section (e.g., curved section 351) defining a deformable preset curvature of penetrator tine 208A and extending in a second direction laterally from the proximal section (e.g., proximal section 350) of penetrator tine 208A and traversing longitudinal axis 212. Penetrator tine 208A may further include a distal section (e.g., distal section 352) extending from the curved section of penetrator tine 208A and terminate in incisive distal end 223. Incisive distal end 223 may be configured to penetrate a tissue to fix IMD 200 to the tissue.

In some examples, base 206 and tines 208 may be integrally formed. For example, base 206 and tines 208 may be integrally formed from a tube, such as a metal tube, a nickel titanium alloy tube, or a stainless-steel tube. In some examples, forming base 206 and tines 208 from a single tube may include removing material from the single tube to define base 206 and tines 208. In some examples, removing material from the single tube may include one or more of machining, chemical etching, laser etching, stamping, or water cutting. In some examples, forming tines 208 may include forming one or more tapers on one or more tines of tines 208. For example, forming one or more tapers may include any other above techniques to remove material from the single tube. In some examples, one or more tapers may be formed while removing material form the single tube.

In some examples, forming tines 208 may include bending each tine of tines 208 to define one or more curved section. In some examples, each curve and/or each tine of tines 208 may be bent individually or bend simultaneously, e.g., by use of a jig configured to bend one or more curves on one or more of tines 208. After bending (and holding in the bent configuration) tines 208, forming tines 208 also may include heat treating the bent tines 208 to cause tines 208 to hold the bent configuration. For example, heat treating the bent tines 208 may cause a microstructure of the material of tines 208 to assume a configuration such that a resting state of tines 208 (e.g., without application of an external force) is the bent configuration.

In some examples, forming tines 208 also may include sharpening distal ends of tines 208. For example, forming penetrator tine 208A may include laser etching distal end 223 of penetrator tine 208A to define an infinitely or near infinitely sharp incisive edge (within the tolerances of common manufacturing processes).

In some examples, forming tines 208 also may include forming one or more cutouts, engravings, embossing, or other variations in the thickness of tines 208. For example, cutouts, engravings, embossing, or other variations in the thickness of tines 208 may be formed by laser etching or chemical etching.

The following examples illustrate example subject matter described herein.

Example 1: An implantable medical device (IMD) includes a body extending from a proximal portion to a distal portion along a longitudinal axis; a fixation component includes a base having a proximal end and a distal end aligned along the longitudinal axis, wherein the proximal end of the base is attached to the distal portion of the body; and a penetrator tine includes a proximal section attached to and extending from the distal end of the base in a first direction; a curved section defining a deformable preset curvature of the penetrator tine and extending in a second direction laterally from the proximal section of the penetrator tine and traversing the longitudinal axis; and a distal section extending from the curved section of the penetrator tine and terminating in an incisive distal end, wherein the incisive distal end is configured to penetrate a tissue to fix the IMD to the tissue; and an electrode interface assembly includes a proximal section defining a proximal end attached to and extending distally from the distal portion of the body along the longitudinal axis; and a distal section extending from the proximal end of the electrode interface assembly and defining a non-incisive distal end, wherein the non-incisive distal end of the electrode interface assembly is configured to contact the tissue to control a depth of tissue penetration of the penetrator tine.

Example 2: The IMD of example 1, wherein, when the curved section of the penetrator tine is in a deployed configuration, a distance between the incisive distal section of the penetrator tine and the non-incisive distal end of the electrode interface assembly is within a range from about 4 millimeters to about 10 millimeters.

Example 3: The IMD of example 1, wherein at least a portion of the electrode interface assembly is configured to urge a leadlet of the IMD toward the penetrator tine.

Example 4: The IMD of example 3, wherein the leadlet comprises an elongate member extending from a proximal end mounted in proximity to a distal end of the body to the incisive distal end of the penetrator tine.

Example 5: The IMD of example 1, wherein the IMD further comprises a leadlet; the leadlet includes elongate member extending from a proximal end mounted in proximity to a distal end of the IMD to the incisive distal end of the penetrator tine; and a first electrode configured to form a first electrical circuit with the tissue and a return electrode on the body of the IMD, wherein the electrode interface assembly further comprises a second electrode positioned at the distal end of the electrode interface assembly, wherein the second electrode is configured to form a second electrical circuit with the tissue and the return electrode.

Example 6: The IMD of example 5, wherein at least one of first electrode or the second electrode is further configured to at least one of deliver stimulation therapy to or sense cardiac signals of a ventricle or an atrium of a heart when the IMD is implanted within an atrium of the heart.

Example 7: The IMD of example 1, wherein a shape of the non-incisive distal end of the electrode interface assembly is substantially bulbous.

Example 8: The IMD of example 1, wherein the deformable preset curvature of the penetrator tine comprises a plurality of curves, each respective curve of the plurality of curves defining a respective radius.

Example 9: The IMD of example 1, wherein the curved section of the penetrator tine further comprises at least one straight segment between two curves of the plurality of curves.

Example 10: The fixation component of example 9, wherein at least a first curve of the plurality of curves of the penetrator tine defines a first radius and a second curve of the plurality of curves of the penetrator tine defines a second radius different than the first radius.

Example 11: The IMD of example 1, wherein the fixation component further comprises one or more support tines, wherein the one or more support tines, when in a deployed configuration, are configured to engage the tissue.

Example 12: The IMD of example 11, wherein the one or more support tines are positioned on the base about 135 degrees from the penetrator tine.

Example 13: The IMD of example 1, wherein the fixation component further comprises one or more guiding tines configured to at least one of control or indicate an orientation of the fixation component during deployment.

Example 14: The IMD of example 13, wherein the one or more guiding tines are positioned on the base about 90 degrees from the penetrator tine.

Example 15: The IMD of example 1, wherein the fixation component further comprises one of more deployment tines configured to increase a deployment force of the fixation component.

Example 16: The IMD of example 15, wherein the one or more deployment tines is at positioned on the base about 45 degree from the penetrator tine.

Example 17: The IMD of example 1, wherein the tissue comprises a myocardium tissue, and wherein the penetrator tine is configured to penetrate at least one of an interatrial septum, an interventricular septum, or an atrioventricular septum.

Example 18: The IMD of example 1, wherein the penetrator tine defines a metal ribbon configured to deform along a plane normal to the longitudinal axis and resist twisting outside of the plane.

Example 19: The IMD of example 1, wherein the incisive distal section of the penetrator tine extends from the curved section of the penetrator tine at an angle within a range from about 45 degrees to about 135 degrees relative to the longitudinal axis.

Example 20: A medical device system includes an implantable medical device (IMD); the IMD includes a body extending from a proximal portion to a distal portion along a longitudinal axis; an elongate leadlet extending from a proximal end of the elongate leadlet mounted in proximity to the distal end of the body to a distal end of the elongate leadlet, wherein the distal end of the elongate leadlet comprises an electrode; a return electrode on the body of the IMD; a fixation component includes a base having a proximal end and a distal end aligned along the longitudinal axis, wherein the proximal end of the base is attached to the distal portion of the body; and a penetrator tine includes a proximal section attached to and extending from the distal end of the base in a first direction; a curved section defining a deformable preset curvature of the penetrator tine and extending in a second direction laterally from the proximal section of the penetrator tine and traversing the longitudinal axis; and a distal section extending from the curved section of the penetrator tine and terminating in an incisive distal end, wherein the incisive distal end is configured to penetrate a tissue to fix the IMD to the tissue; and an electrode interface assembly includes a proximal section defining a proximal end attached to and extending distally from the distal portion of the body along the longitudinal axis; and a distal section extending from the proximal end of the electrode interface assembly and defining a non-incisive distal end, wherein the non-incisive distal end of the electrode interface assembly is configured to contact the tissue to control a depth of tissue penetration of the penetrator tine; and a delivery tool comprising a tubular sidewall that defines a lumen into which the IMD may be loaded, wherein the lumen has a distal opening through which the IMD may be deployed.

Example 21: The medical device system of example 20, wherein the electrode comprises a first electrode configured to form a first electrical circuit with the tissue and a return electrode on the body of the IMD, and wherein the electrode interface assembly further comprises a second electrode positioned at the distal end of the electrode interface assembly, wherein the second electrode is configured to form a second electrical circuit with the tissue and the return electrode.

Example 22: The IMD of example 21, wherein at least one of first electrode or the second electrode is further configured to at least one of deliver stimulation therapy to or sense cardiac signals of a ventricle or an atrium of a heart when the IMD is implanted within an atrium of the heart.

Example 23: The IMD of example 20, wherein, when the curved section of the penetrator tine is in a deployed configuration, a distance between the incisive distal section of the penetrator tine and the non-incisive distal end of the electrode interface assembly is within a range from about 4 millimeters to about 10 millimeters.

Example 24: The IMD of example 20, wherein at least a portion of the electrode interface assembly is configured to urge the elongate leadlet toward the penetrator tine.

Example 25: The IMD of example 20, wherein the elongate leadlet extends from a proximal end mounted in proximity to a distal end of the body to the incisive distal end of the penetrator tine.

Example 26: A method of forming an IMD includes forming a body of the IMD, wherein the body extends from a proximal portion to a distal portion along a longitudinal axis; attaching an electrode interface assembly to the distal portion of the body, wherein the electrode interface assembly comprises: a proximal section defining a proximal end attached to and extending distally from the distal portion of the body along the longitudinal axis; and a distal section extending from the proximal section of the electrode interface assembly and defining a non-incisive distal end, attaching a fixation component to the distal portion of the body, wherein the fixation component comprises: a base having a proximal end and a distal end aligned along the longitudinal axis, wherein the proximal end of the base is attached to the distal portion of the body; and a penetrator tine includes a proximal section attached to and extending from the distal end of the base in a first direction; a curved section defining a deformable preset curvature of the penetrator tine and extending in a second direction laterally from the proximal section of the penetrator tine and traversing the longitudinal axis; and a distal section extending from the curved section of the penetrator tine and terminating in an incisive distal end, wherein the incisive distal end is configured to penetrate a tissue to fix the IMD to the tissue, wherein the non-incisive distal end of the electrode interface assembly is configured to contact the tissue to control a depth of tissue penetration of the penetrator tine.

Example 27: The method of example 26, wherein the method further comprises forming the fixation component.

Example 28: The method of example 27, wherein forming the fixation component comprises forming the penetrator tine to include at least one of a cutout, an engraving, an embossing, or variation in thickness of the penetrator tine.

Example 29: The method of example 26, wherein the method further comprises forming the electrode interface assembly to urge, by at least a portion of the electrode interface assembly, a leadlet of the IMD toward the penetrator tine, wherein the leadlet comprises a first electrode.

Example 30: The method of example 26, wherein forming the electrode interface assembly further comprises forming the electrode interface assembly to define a passage configured to receive therein a second electrode.

Example 31: The method of example 26, wherein, when the curved section of the penetrator tine is in a deployed configuration, a distance between the distal section of the penetrator tine and the distal end of the electrode interface assembly is within a range from about 4 millimeters to about 10 millimeters.

Various examples of the disclosure have been described. Any combination of the described systems, operations, or functions is contemplated. These and other examples are within the scope of the following claims.

What is claimed is:
1. An implantable medical device (IMD), comprising:
   a body extending from a proximal portion to a distal portion along a longitudinal axis;
   a fixation component comprising:

a base having a proximal end and a distal end aligned along the longitudinal axis, wherein the proximal end of the base is attached to the distal portion of the body; and a penetrator tine comprising:
 a proximal section attached to and extending from the distal end of the base in a first direction;
 a curved section defining a deformable preset curvature of the penetrator tine and extending in a second direction laterally from the proximal section of the penetrator tine and traversing the longitudinal axis; and
 a distal section extending from the curved section of the penetrator tine and terminating in an incisive distal end, wherein the incisive distal end is configured to penetrate a tissue to fix the IMD to the tissue; and an electrode interface assembly separate from the body and coupled to the body, the electrode interface assembly comprising:
 a proximal section defining a proximal end, wherein the proximal end is configured to be attached to and extending distally from the distal portion of the body along the longitudinal axis; and
 a distal section extending from the proximal end of the electrode interface assembly and defining a non-incisive distal end, wherein when the electrode interface assembly is coupled to the body, the non-incisive distal end of the electrode interface assembly is configured to contact the tissue to control a depth of tissue penetration of the penetrator tine.

2. The IMD of claim 1, wherein, when the curved section of the penetrator tine is in a deployed configuration, a distance between the incisive distal end of the penetrator tine and the non-incisive distal end of the electrode interface assembly is within a range from about 4 millimeters to about 10 millimeters.

3. The IMD of claim 1, wherein at least a portion of the electrode interface assembly is configured to urge a leadlet of the IMD toward the penetrator tine.

4. The IMD of claim 3, wherein the leadlet comprises an elongate member extending from a proximal end mounted in proximity to a distal end of the body to the incisive distal end of the penetrator tine.

5. The IMD of claim 1, wherein the IMD further comprises a leadlet comprising:
 an elongate member extending from a proximal end mounted in proximity to a distal end of the IMD to the incisive distal end of the penetrator tine; and
 a first electrode configured to form a first electrical circuit with the tissue and a return electrode on the body of the IMD,
 wherein the electrode interface assembly further comprises a second electrode positioned at the distal end of the electrode interface assembly, wherein the second electrode is configured to form a second electrical circuit with the tissue and the return electrode.

6. The IMD of claim 5, wherein at least one of first electrode or the second electrode is further configured to at least one of deliver stimulation therapy to or sense cardiac signals of a ventricle or an atrium of a heart when the IMD is implanted within an atrium of the heart.

7. The IMD of claim 1, wherein a shape of the non-incisive distal end of the electrode interface assembly is substantially bulbous.

8. The IMD of claim 1, wherein the deformable preset curvature of the penetrator tine comprises a plurality of curves, each respective curve of the plurality of curves defining a respective radius.

9. The IMD of claim 8, wherein the curved section of the penetrator tine further comprises at least one straight segment between two curves.

10. The fixation component of claim 9, wherein at least a first curve of the penetrator tine defines a first radius and a second curve of the penetrator tine defines a second radius different than the first radius.

11. The IMD of claim 1, wherein the fixation component further comprises one or more support tines, wherein the one or more support tines, when in a deployed configuration, are configured to engage the tissue.

12. The IMD of claim 11, wherein the one or more support tines are positioned on the base about 135 degrees from the penetrator tine.

13. The IMD of claim 1, wherein the fixation component further comprises one or more guiding tines configured to at least one of control or indicate an orientation of the fixation component during deployment.

14. The IMD of claim 13, wherein the one or more guiding tines are positioned on the base about 90 degrees from the penetrator tine.

15. The IMD of claim 1, wherein the fixation component further comprises one of more deployment tines configured to increase a deployment force of the fixation component.

16. The IMD of claim 15, wherein the one or more deployment tines is at positioned on the base about 45 degree from the penetrator tine.

17. The IMD of claim 1, wherein the tissue comprises a myocardium tissue, and wherein the penetrator tine is configured to penetrate at least one of an interatrial septum, an interventricular septum, or an atrioventricular septum.

18. The IMD of claim 1, wherein the penetrator tine defines a metal ribbon configured to deform along a plane normal to the longitudinal axis and resist twisting outside of the plane.

19. The IMD of claim 1, wherein the incisive distal end of the penetrator tine extends from the curved section of the penetrator tine at an angle within a range from about 45 degrees to about 135 degrees relative to the longitudinal axis.

20. A medical device system comprising:
 an implantable medical device (IMD), comprising:
  a body extending from a proximal portion to a distal portion along a longitudinal axis;
  an elongate leadlet extending from a proximal end of the elongate leadlet mounted in proximity to a distal end of the body to a distal end of the elongate leadlet, wherein the distal end of the elongate leadlet comprises an electrode;
  a return electrode on the body of the IMD;
  a fixation component comprising:
   a base having a proximal end and a distal end aligned along the longitudinal axis, wherein the proximal end of the base is attached to the distal portion of the body; and
   a penetrator tine comprising:
    a proximal section attached to and extending from the distal end of the base in a first direction;
    a curved section defining a deformable preset curvature of the penetrator tine and extending in a second direction laterally from the proximal section of the penetrator tine and traversing the longitudinal axis; and a distal section extending from the curved section of the penetrator tine and terminating in an incisive distal end, wherein the incisive distal end is configured to penetrate a tissue to fix the IMD to the tissue; and an electrode interface assembly comprising:
  a proximal section defining a proximal end attached to and extending distally from the distal portion of the body along the longitudinal axis; and
  a distal section extending from the proximal end of the electrode interface assembly and defining a non-incisive distal end, wherein the non-incisive distal end of the electrode interface assembly is configured to contact the tissue to control a depth of tissue penetration of the penetrator tine; and a delivery tool comprising a tubular sidewall that defines a lumen configured to receive the IMD, wherein the lumen has a distal opening through which the IMD may be deployed.

21. A method of forming an IMD comprising:

forming a body of the IMD, wherein the body extends from a proximal portion to a distal portion along a longitudinal axis;

attaching an electrode interface assembly to the distal portion of the body, wherein the electrode interface assembly is formed separated from the body, and wherein the electrode interface assembly comprises:
  a proximal section defining a proximal end attached to and extending distally from the distal portion of the body along the longitudinal axis; and
  a distal section extending from the proximal section of the electrode interface assembly and defining a non-incisive distal end;

attaching a fixation component to the distal portion of the body, wherein the fixation component comprises:
  a base having a proximal end and a distal end aligned along the longitudinal axis, wherein the proximal end of the base is attached to the distal portion of the body; and
  a penetrator tine comprising:
    a proximal section attached to and extending from the distal end of the base in a first direction;
    a curved section defining a deformable preset curvature of the penetrator tine and extending in a second direction laterally from the proximal section of the penetrator tine and traversing the longitudinal axis; and
    a distal section extending from the curved section of the penetrator tine and terminating in an incisive distal end, wherein the incisive distal end is configured to penetrate a tissue to fix the IMD to the tissue, wherein the non-incisive distal end of the electrode interface assembly is configured to contact the tissue to control a depth of tissue penetration of the penetrator tine.

22. The method of claim 21, wherein forming the electrode interface assembly further comprises forming the electrode interface assembly to define a passage configured to receive therein an electrode.

* * * * *